United States Patent [19]

Liu et al.

[11] Patent Number: 5,914,230
[45] Date of Patent: *Jun. 22, 1999

[54] HOMOGENEOUS AMPLIFICATION AND DETECTION OF NUCLEIC ACIDS

[75] Inventors: Yen Ping Liu, Cupertino; Rajesh D. Patel, Fremont; Nurith Kurn; Claire Lin, both of Palo Alto; Samuel J. Rose, Los Altos; Edwin F. Ullman, Atherton, all of Calif.

[73] Assignee: Dade Behring Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/771,624

[22] Filed: Dec. 20, 1996

Related U.S. Application Data

[60] Provisional application No. 60/009,090, Dec. 22, 1995.

[51] Int. Cl.⁶ .............................. C12Q 1/68; C12P 19/34
[52] U.S. Cl. .............................................. 435/6; 435/91.2
[58] Field of Search ................................ 536/24.3, 24.5; 435/6, 91.2

[56] References Cited

U.S. PATENT DOCUMENTS

| | | | |
|---|---|---|---|
| 4,868,104 | 9/1989 | Kurn et al. | 435/6 |
| 5,474,895 | 12/1995 | Ishii et al. | 435/6 |
| 5,624,803 | 4/1997 | Noonberg et al. | 435/6 |
| 5,681,697 | 10/1997 | Urdea et al. | 435/6 |
| 5,753,439 | 5/1998 | Smith et al. | 435/6 |

FOREIGN PATENT DOCUMENTS

| | | |
|---|---|---|
| 070687A2 | 1/1983 | European Pat. Off. . |
| 144914A2 | 6/1985 | European Pat. Off. . |
| 232967B1 | 8/1987 | European Pat. Off. . |
| WO 8606412 | 11/1986 | WIPO . |
| WO 93/10267 | 5/1993 | WIPO . |
| WO 9402634 | 2/1994 | WIPO . |
| WO 9707235 | 2/1997 | WIPO . |

OTHER PUBLICATIONS

Morrison et al; *Anal Biochem*; 183; pp. 231–244; Solution–Phase Dection of Polynucleotide Using Interacting Fluorescent Labels and Competitive Hybridization; 1989.

Oser et al; *Angew Chem Int Ed Engl*; 29:10; 1167; Nonradioactive Assay of DNA Hybridization by DNA–Template–Mediated Formation of a Ternary Tb(III) Complex in Pure Liquid Phase; 1990.

Ullman et al.; *Clin Chem*; 42:9; 1518–1526; Luminescent Oxygen Channeling Assay (LOCI™): Sensitive, Broadly Applicable Homogeneous Immunoassay Method; 1996.

Ullman et al.; *Proc Natl Acad Sci*; 91:5426–5430; Luminescent Oxygen Channeling Assay: Measurement of Particle Binding Kinetics by Chemiluminescence; Jun. 1994.

*Primary Examiner*—Nancy Degen
*Assistant Examiner*—Irem Yucel
*Attorney, Agent, or Firm*—Theodore J Leitereg

[57] ABSTRACT

The present invention relates to a method for detecting or amplifying and detecting a target polynucleotide sequence. The method comprises providing in combination (i) a medium suspected of containing the target polynucleotide sequence, (ii) all reagents required for conducting an amplification of the target polynucleotide sequence when amplification is desired, and (iii) two oligonucleotide probes capable of binding to a single strand of the product of the amplification. At least one of the probes has two sequences that either (i) are non-contiguous and bind to contiguous or non-contiguous sites on the single strand or (ii) can bind to non-contiguous sites on the single strand. Each probe may contain a label. The combination is subjected to conditions for amplifying the target polynucleotide sequence. Next, the combination is subjected to conditions under which both of the probes hybridize to one of the strands to form a termolecular complex, which is detected by means of the label.

53 Claims, 4 Drawing Sheets

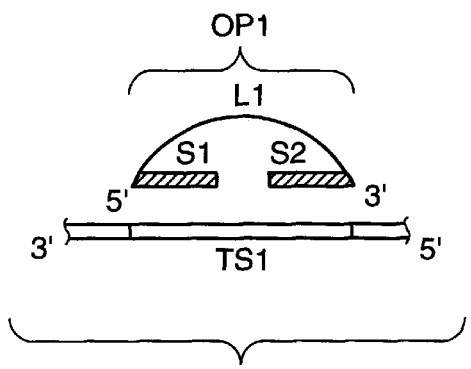
FIG._1
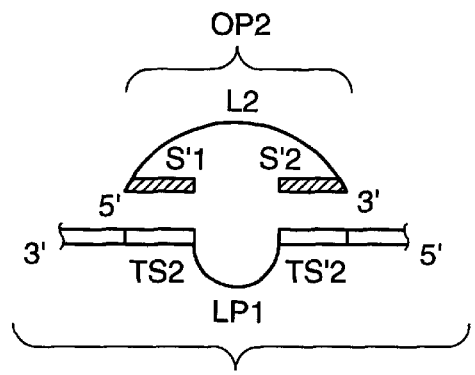
FIG._2
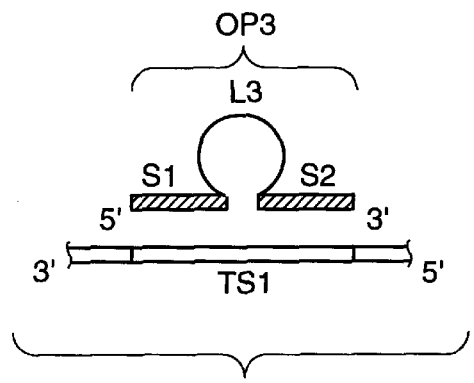
FIG._3
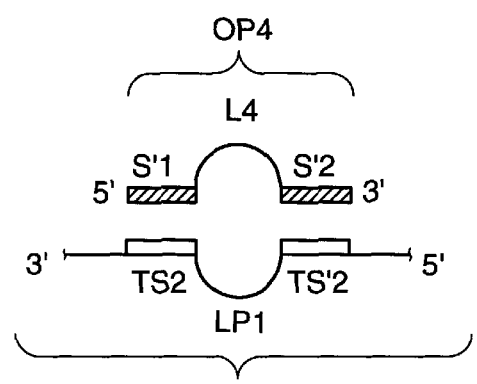
FIG._4
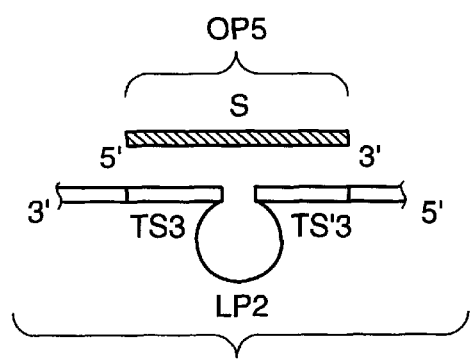
FIG._5

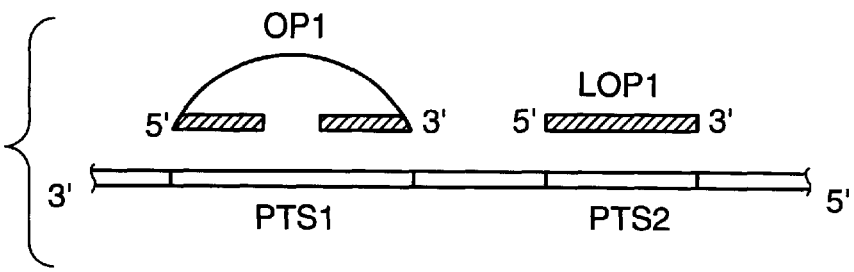
FIG._6
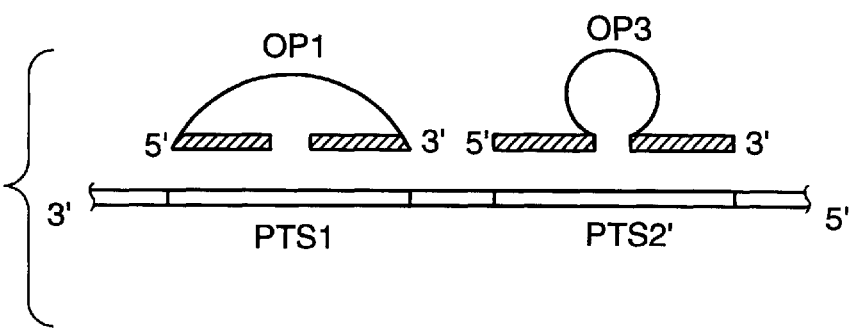
FIG._7
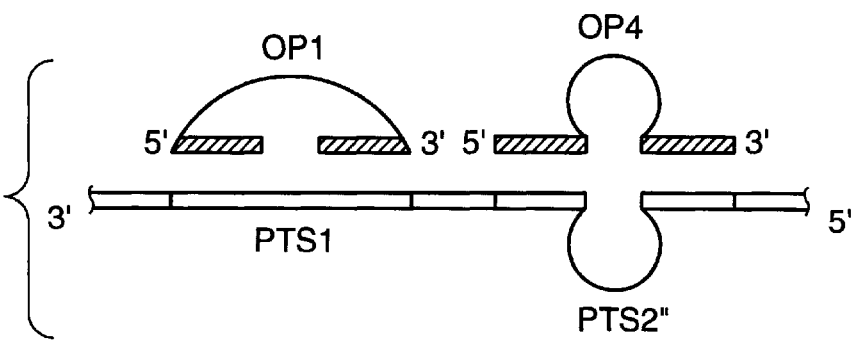
FIG._8
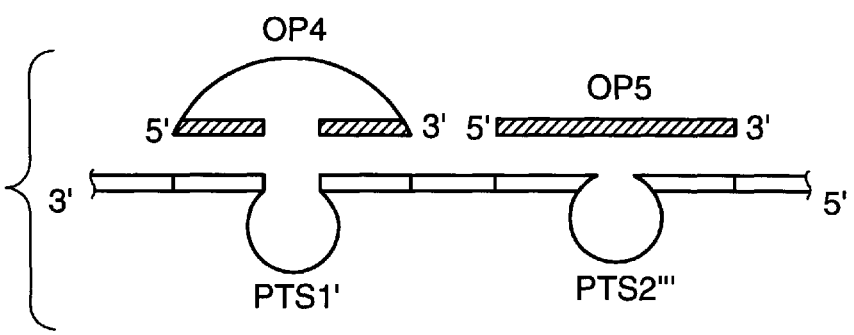
FIG._9

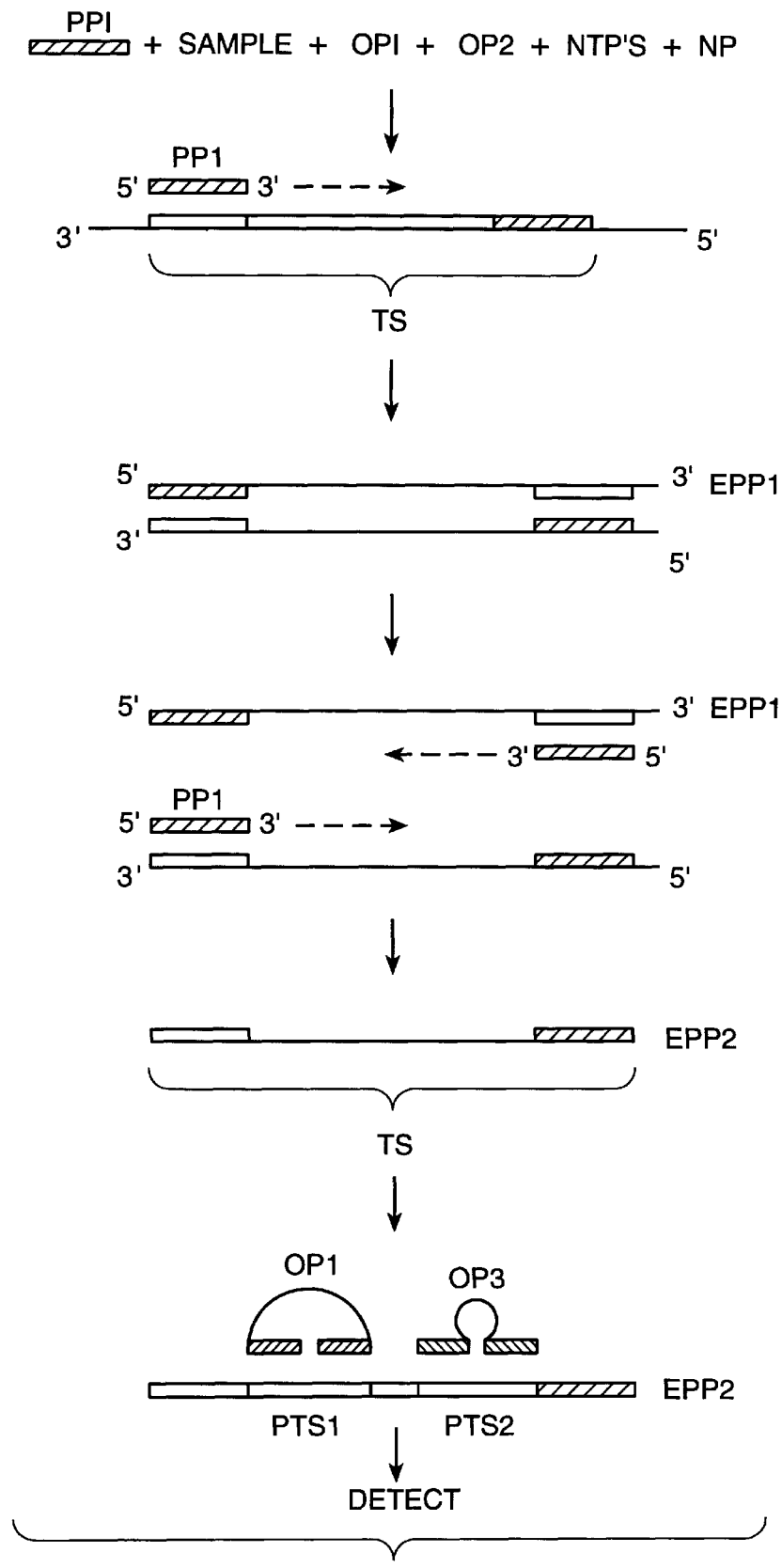
FIG._10

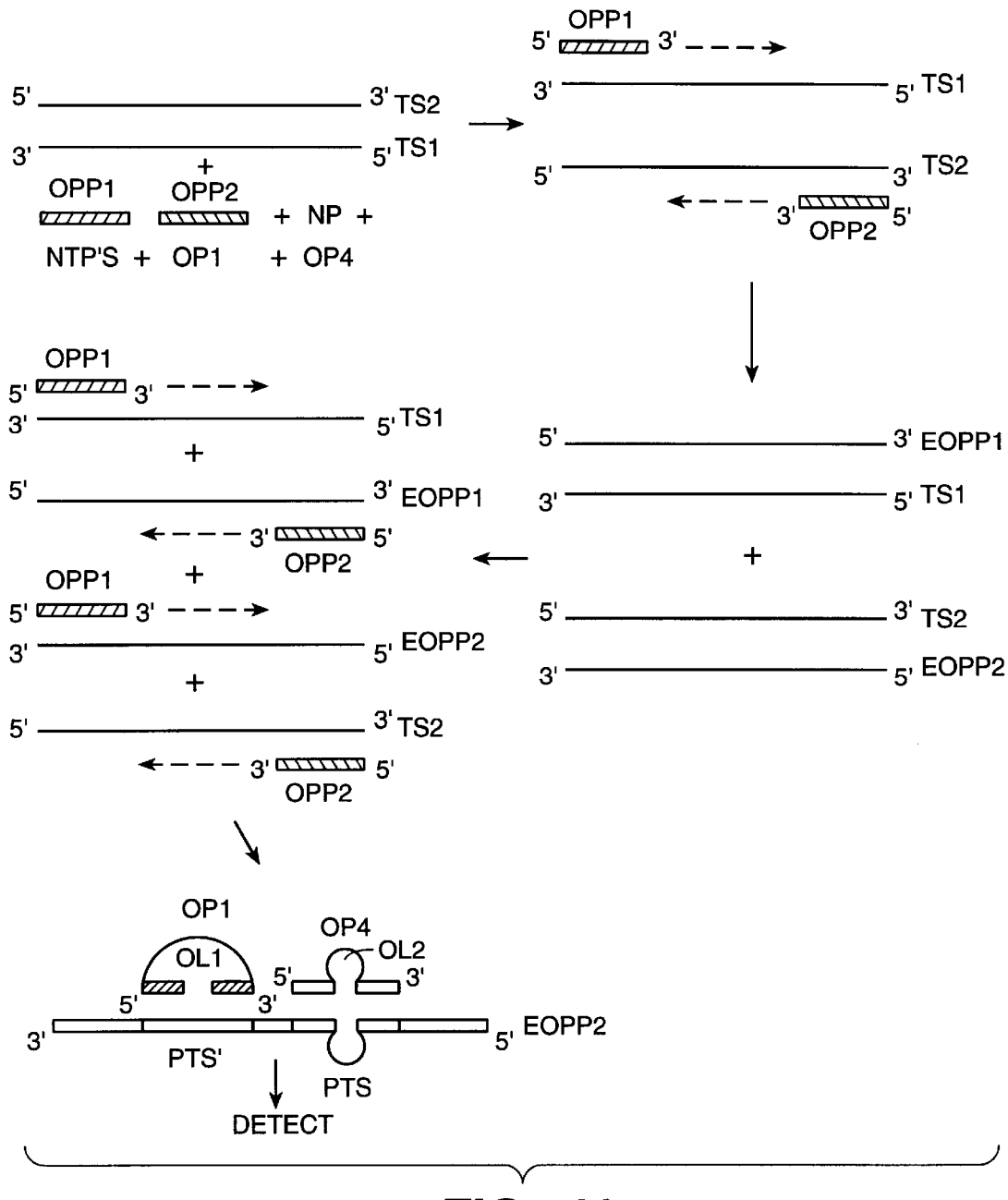
FIG._11

```
                            SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:1:

TTTTTTTTTT TTTTTTTTTT TTTTTTTTTT TTTTTTTTTT                            40

(2) INFORMATION FOR SEQ ID NO:2:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:2:

TCATGGTTCT GGTCAGGTGC AGAT                                             24
```

(2) INFORMATION FOR SEQ ID NO:3:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:3:

TCATGGTTCT GGTCAGGTGC AGATTTACCG CGCATACGGA ATAGCTTACC GGTCT    55

(2) INFORMATION FOR SEQ ID NO:4:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:4:

CGCTCGAAAA TCGGGAAAAA AAAAAAAAAA AAAAAAAAAA TGACGGGACT TCGC    54

(2) INFORMATION FOR SEQ ID NO:5:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:5:

CAACACGACC ATGACCTAAT CCTAATCCTA ATCCTAATCG GATTTTAACG GACA    54

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal

```
        (xi) SEQUENCE DESCRIPTION: SEQ ID NO:6:

GATTAGGATT AGGATTAGGA TTAGGATTAG GATTAGGATT AG                    42

(2) INFORMATION FOR SEQ ID NO:7:

(i) SEQUENCE CHARACTERISTICS:
          (A) LENGTH: 53 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:7:

CAACACGACC ATGACCTAAT CCTAATCCTA ATCCTAATCG GATTTTAACG GAC         53

(2) INFORMATION FOR SEQ ID NO:8:

(i) SEQUENCE CHARACTERISTICS:
          (A) LENGTH: 55 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:8:

TTCGATTTCG CCACCAAAAA AAAAAAAAAA AAAAAAAAAA TGATCGGGAC TTCGC       55

(2) INFORMATION FOR SEQ ID NO:9:

(i) SEQUENCE CHARACTERISTICS:
          (A) LENGTH: 54 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:9:

GATGCGGTCT CCAGTCTAAT CCTAATCCTA ATCCTAATCG GATTTTAACG GACA        54

(2) INFORMATION FOR SEQ ID NO:10:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO
```

-continued (iv) ANTI-SENSE: NO (v) FRAGMENT TYPE: C-terminal (xi) SEQUENCE DESCRIPTION: SEQ ID NO:10:

AAAAAAAAAA AAAAAAAAAA AAAAATTATC GGGACTTCGC                              40

(2) INFORMATION FOR SEQ ID NO:11:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:11:

CTAATCCTAA TCCTAATCCT AATCGGATTT TAACGGACA                               39

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:12:

CAAAACAGCG GAAGAGCGTG AAATC                                              25

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:13:

GGATGCGGTC TCCAGTGTCC A                                                  21

(2) INFORMATION FOR SEQ ID NO:14:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:14:

CAAAACAGCG GAAGAGCGTG AAATC                                                  25

(2) INFORMATION FOR SEQ ID NO:15:

(i) SEQUENCE CHARACTERISTICS:
             (A) LENGTH: 75 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:15:

CAAAACAGCG GAAGAGCGTG AAATCGGCCC TGACATGTCA GGGCCGCGGT ACGCTGATCA            60

AAGATCCGTG CAACA                                                             75

(2) INFORMATION FOR SEQ ID NO:16:

(i) SEQUENCE CHARACTERISTICS:
             (A) LENGTH: 47 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:16:

TCTGCACCTG ACCAGCTTAA TCCTAATCCT AATCTACAGC GAAGAAT                          47

(2) INFORMATION FOR SEQ ID NO:17:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:17:

GACGGTTGGA TGCCTGCCTC GG                                                     22

(2) INFORMATION FOR SEQ ID NO:18:

(i) SEQUENCE CHARACTERISTICS:
    (A) LENGTH: 67 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:18:

GACGGTTGGA TGCCTGCCTC GGTAACCCTG AATTCAGGGT TAGCCACACT TTGCGGGCAC    60

CGTAAAC    67

(2) INFORMATION FOR SEQ ID NO:19:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:19:

GGGTAGCAGA CCTCACCTAG AGAATCCTAA TCCTAATCCA CAACCACCAG CACCTAACCG    60

G    61

(2) INFORMATION FOR SEQ ID NO:20:

(i) SEQUENCE CHARACTERISTICS:
       (A) LENGTH: 64 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:20:

ACGGATAGGG GATCTCAGTA GACTTTTTTT TTTTTTTTTT TTACGTACTC GACCTGAAAG    60

ACGT    64

(2) INFORMATION FOR SEQ ID NO:21:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:21:

GCGTACTCGA CCTGAAAGTT TTTTTTTTTT TTTTTTTT                               38

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:22:

ACTGGTAGAG GCGGCGATGG TTGAA                                             25

(2) INFORMATION FOR SEQ ID NO:23:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:23:

AGCAGACCTC ACCTACTAAT CCTAATCCTA ATCCTAATCA CCACCAGCAC CTAA              54

(2) INFORMATION FOR SEQ ID NO:24:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:24:

ATAGGGGATC TCAGTAAAAA AAAAAAAAAA AAAAAAAAT ACTCGACCTG AAAG               54

HOMOGENEOUS AMPLIFICATION AND DETECTION OF NUCLEIC ACIDS

This application claims benefit of provisional application Ser. No. 60/009,090, filed Dec. 22, 1995.

BACKGROUND OF THE INVENTION

1. Field of the Invention.

Significant morbidity and mortality are associated with infectious diseases. More rapid and accurate diagnostic methods are required for better monitoring and treatment of disease. Molecular methods using DNA probes, nucleic acid hybridizations and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labeling of DNA with T4 polynucleotide kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

One method for detecting specific nucleic acid sequences generally involves immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the above method is slow and labor intensive, and nonisotopic labels that are less readily detected than radiolabels are frequently not suitable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Other methods for amplifying nucleic acids are single primer amplification, ligase chain reaction (LCR), nucleic acid sequence based amplification (NASBA) and the Q-beta-replicase method. Regardless of the amplification used, the amplified product must be detected.

For any of the above methods for amplifying nucleic acid there is a risk of contaminating the amplification mixture with previously amplified material and thereby amplifying material that was not present in the original sample, namely, a contaminant. The quantities of amplification product can be very large thereby aggravating the potential contamination. Once aerosols of amplified nucleic acid are produced in a laboratory, droplets containing this material can invade subsequent amplification mixtures or equipment. Attempted amplification of a nucleic acid may then produce amplified copies of this contaminating material even when the target nucleic acid, or sequence thereof, was not present in the sample being amplified. Such contamination can also occur if the same container is employed for multiple amplifications even though the container is cleaned. As few as one molecule will sometimes be sufficient to contaminate other containers that are to be used in further amplifications. This possibility for contamination can result in a false test since such a single molecule can be amplified and detected. The result of the test will not accurately reflect the presence or absence of the particular nucleic acid in the patient sample being tested.

After amplification of a particular nucleic acid, a separate step is carried out prior to detecting amplified material. One method for detecting nucleic acids is to employ nucleic acid probes. One method utilizing such probes is described in U.S. Pat. No. 4,868,104. A nucleic acid probe may be, or may be capable of being, labeled with a reporter group or may be, or may be capable of becoming, bound to a support. Detection of signal depends upon the nature of the label or reporter group. If the label or reporter group is an enzyme, additional members of the signal producing system include enzyme substrates and so forth.

It is desirable to have a sensitive, simple method for amplifying and detecting nucleic acids preferably, in a homogeneous format. The method should minimize the number and complexity of steps and reagents. The need for sterilization and other steps needed to prevent contamination of assay mixtures should be avoided.

2. Description of the Related Art.

Rapid, non-separation electrochemiluminescent DNA hybridization assays for PCR products using 3'-labeled oligonucleotide probes is described by Gudibande, et al., (1992) *Molecular and Cellular Probes*, 6: 495–503. A related disclosure is found in international patent application WO 9508644 A1 (950330).

Marmaro, et al.,(Meeting of the American Association of Clinical Chemists, San Diego, Calif., November 1994, Poster No. 54) discusses the design and use of fluorogenic probes in TaqMan, a homogeneous PCR assay.

A PCR-based assay that utilizes the inherent 5' nuclease of rTth DNA polymerase for the quantitative detection of HCV RNA is disclosed by Tsang, et al., (94th General Meeting of the American Society for Microbiology, Las Vegas Nev. 5/94, Poster No. C376).

Kemp, et al., (1990) *Gene*, 94:223–228, disclose simplified colorimetric analysis of polymerase chain reactions and detection of HIV sequences in AIDS patients.

German patent application DE 4234086-A1 (92.02.05) (Henco, et al.) discusses the determination of nucleic acid sequences amplified in vitro in enclosed reaction zone where probe(s) capable of interacting with target sequence is present during or after amplification and spectroscopically measurable parameters of probe undergo change thereby generating signal.

U.S. Pat. No. 5,232,829 (Longiaru, et al.) discloses detection of chlamydia trachomatis by polymerase chain reaction using biotin labeled DNA primers and capture probes. A similar disclosure is made by Loeffelholz, et al. (1992) *Journal of Clinical Microbiology*, 30(11):2847–2851.

Padlock probes: circularizing oligonucleotides for localized DNA detection are described by Nilsson, et al. (1994) *Science*, 265:2085–2088.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science*, 230: 1350–1354. Primer-directed enzymatic amplification of DNA with a thermostable DNA polymerase is described by Saiki, et al., *Science* (1988) 239:487.

U.S. patent application Ser. Nos. 07/299,282 and 07/399,795, filed Jan. 19, 1989, and Aug. 29, 1989, respectively, describe nucleic acid amplification using a single polynucleotide primer (ASPP). U.S. patent application Ser. No. 07/555,323 filed Jul. 19, 1990, discloses methods for producing a polynucleotide for use in single primer amplification. U.S. patent application Ser. No. 07/555,968 describes a method for producing a molecule containing an intramolecular base-pair structure. A method for producing a polynucleotide for use in single primer amplification is described in U.S. patent application Ser. No. 07/776,538 filed Oct. 11, 1991. A method for introducing defined sequences at the 3'-end of a polynucleotide is described in U.S. patent application Ser. No. 08/140,369, filed Oct. 20, 1993. The disclosures of these six applications are incorporated herein by reference including the references listed therein in the sections entitled "Description of the Related Art."

SUMMARY OF THE INVENTION

One embodiment of the present invention is a method for detecting a target polynucleotide sequence. The method comprises combining the target polynucleotide sequence with two probes that are capable of binding to the same strand of the target polynucleotide sequence to form a termolecular complex. At least one of the probes has two sequences that are non-contiguous and can bind to contiguous or non-contiguous sites on a single strand of the target polynucleotide sequence. The termolecular complex is then detected.

One embodiment of the present invention relates to a method for amplifying and detecting a target polynucleotide sequence. The method comprises providing in combination (i) a medium suspected of containing the target polynucleotide sequence, (ii) all reagents required for conducting an amplification of the target polynucleotide sequence when an amplification is desired, and (iii) two oligonucleotide probes capable of binding to a single strand of the product of the amplification. At least one of the probes has two sequences that are non-contiguous and/or can bind to non-contiguous sites on the single strand. Each probe may contain a label. The combination is subjected to conditions for amplifying the target polynucleotide sequence. Next, the combination is subjected to conditions under which both of the probes hybridize to one of the strands to form a termolecular complex, which is detected by means of the label.

An aspect of the present invention relates to a method for amplifying and detecting a target polynucleotide sequence. In the method a combination is provided comprising a sample suspected of containing a target polynucleotide having the target polynucleotide sequence, reagents for amplifying the target polynucleotide sequence to produce copies thereof, a first oligonucleotide probe and a second oligonucleotide probe. The copies are not substantially hybridized to the probes during the amplification. Subsequent to the amplification both of the probes hybridize to one of the strands of the copies. Each of the probes is comprised of a label that facilitates detection of the probes hybridized to the strands. The combination is subjected to conditions for amplifying the target polynucleotide sequence to produce the copies. Next, the combination is subjected to conditions under which the probes hybridize to one of the strands to form a termolecular complex. The complex is then detected usually by irradiation of the combination with light and detecting the emission of light from the combination following termination of the irradiation.

Another embodiment of the present invention is a method for amplifying and detecting a target polynucleotide sequence of a polynucleotide analyte. A combination is provided which comprises a sample suspected of containing a polynucleotide analyte having the target polynucleotide sequence, reagents for amplifying the polynucleotide analyte to produce copies of the target polynucleotide sequence, a first oligonucleotide probe having nucleotide sequences S1 and S2 and a second oligonucleotide probe having sequences S3 and S4. The sequences comprising at least one of the probes are linked such that either (i) they are non-contiguous and bind to contiguous or non-contiguous sites on one of the strands of the copies or (ii) the sites to which they hybridize on one of the strands of the copies are non-contiguous. The probes do not substantially hybridize to the copies during the amplification and preferably do not interfere with the amplification. Subsequent to the amplification, both of the probes can hybridize to one of the strands of the copies. Each of the probes is comprised of a label that facilitates detection of the probes hybridized to the strands. The combination is subjected to conditions for amplifying the polynucleotide analyte. Next, the combination is subjected to conditions under which both of the probes hybridize to one of the strands to form a termolecular complex. The method further comprises detecting the complex comprising the probes hybridized to the strands.

Another embodiment of the present invention is directed to a method of detecting a target polynucleotide containing a target polynucleotide sequence wherein all reagents required for the method are first combined with the target polynucleotide. The method comprises dissociating the target polynucleotide sequence into single strands when the target polynucleotide sequence is double stranded. An oligonucleotide primer is hybridized to the 3'-end of each of the single strands. The primers hybridized to each of the single strands is extended along the single strands to produce a copy of the target polynucleotide sequence. The copy is dissociated into single strands. Then, two oligonucleotide probes are hybridized to one of the single strands. At least one of the probes is comprised of two sequences that hybridize with one of the single strands. The sequences are non-contiguous and bind to contiguous or non-contiguous sites on the strand or the sites on the strand to which the sequences hybridize are non-contiguous. The binding of both of the probes to the single strands is detected and the presence of such binding is related to the presence of the target polynucleotide.

Another embodiment of the present invention is a method for detecting a target sequence of a target polynucleotide ("target sequence"). The method comprises amplifying the target sequence by primer extension and detecting extended primer. In particular, the amplification of the target sequence is carried out by a method comprising: (i) hybridizing to the 3'-end of the target sequence a first oligonucleotide primer ("first primer"), extending, in the presence of a polymerase and nucleotide triphosphates, the first primer along at least the target sequence to produce an extended first primer, the first primer being capable of hybridizing to, and being extended along, (1)extended first primer or (2) an extended second oligonucleotide primer ("second primer") wherein the extended second primer results from the extension of a second primer capable of hybridizing to and extending along a polynucleotide that is complementary (complementary polynucleotide) to the target sequence, (iii) dissociating the extended first primer from the target sequence, (iv) hybridizing, to the 3'-end of the extended first primer, the first or the second primer, (v) extending the first or the second primer along the extended first primer, (vi) dissociating the extended first primer or the extended second primer from the extended first primer, (vii) hybridizing, to the 3'-end of the extended first or the extended second primer, the first primer, and (viii) repeating steps (v)–(vii). Detection of the extended first primer and/or the extended second primer is accomplished by means of a first oligonucleotide probe having nucleotide sequences S1 and S2 and a second oligonucleotide probe having sequences S3 and S4. The sequences comprising at least one of the probes are linked such that either (i) its two sequences are non-contiguous and bind to contiguous or non-contiguous sites on one of the extended primers or (ii) the sites to which they hybridize on one of the extended primers are non-contiguous. The probes are present during the amplification, do not substantially hybridize to the extended first and/or second primers during the amplification and do not interfere with the amplification. Subsequent to amplifying, both of the probes can hybridize to one of the extended first and/or the extended second primers and in such a way form a termolecular complex. One or both of the probes contains a label that facilitates detection of the probes hybridized to the extended first and/or the extended second primers.

Another embodiment of the present invention relates to a kit for use in amplification and detection of a target polynucleotide sequence. The kit is a packaged combination of (a) reagents for conducting an amplification of the target polynucleotide sequence comprising two oligonucleotides capable of binding to the sequence and an enzyme capable of modifying at least one of the oligonucleotides as a function of the presence of the sequence, and (b) two oligonucleotide probes capable of binding to a single strand of the product of the amplification wherein at least one of the probes has two sequences that either (i) are non-contiguous and can bind to contiguous or non-contiguous sites on the single strand or (ii) can bind to non-contiguous sites on the single strand and each probe contains a label. Each of the probes may comprise particles capable of binding to the label. The kit may also comprise a second particle bound to or capable of binding to the other of the probes. Exemplary reagents for conducting an amplification comprise (a) nucleotide triphosphates, (b) an oligonucleotide primer and (c) a nucleotide polymerase.

Another embodiment of the present invention relates to kits for use in an amplification and detection of a target polynucleotide sequence of a target polynucleotide. A kit in accordance with the instant invention comprises, in packaged combination, (a) an oligonucleotide primer which is hybridizable to the target polynucleotide and is extendable along the target polynucleotide sequence to produce extended oligonucleotide primer, (b) nucleoside triphosphates, (c) a nucleotide polymerase, (d) a first oligonucleotide probe having nucleotide sequences S1 and S2, and (e) a second oligonucleotide probe having sequences S3 and S4. The sequences comprising at least one of the first or the second oligonucleotide probes are linked such that either (i) they are non-contiguous and bind to contiguous or non-contiguous sites on the extended primer or a complementary thereto or (ii) the sites to which they hybridize on the extended polynucleotide primer or a complementary sequence thereto are non-contiguous. The probes have the characteristics that they (i) do not substantially hybridize to the extended oligonucleotide primer during the amplification and (ii) subsequent to the amplification, both of the first and second oligonucleotide probes can hybridize to the extended oligonucleotide primer or the complementary sequenced, and (iii) one or both of the probes contain a label that facilitates detection of the probes hybridized to the extended oligonucleotide primer or the complementary sequence.

Another method in accordance with the present invention for amplifying and detecting a target polynucleotide sequence comprises providing in combination a sample suspected of containing a target polynucleotide having the target polynucleotide sequence, reagents for amplifying the target polynucleotide sequence to produce copies thereof, a first oligonucleotide probe and a second oligonucleotide probe. The probes do not substantially hybridize to the copies during the amplifying and do not interfere with the amplifying. Subsequent to the amplifying, both of the probes can hybridize to one of the strands of the copies. At least one the probes is associated with a particle. The combination is subjected to conditions for amplifying the target polynucleotide sequence to produce the copies. Thereafter, the combination is subjected to conditions under which both of the probes hybridize to one of the strands and result in agglutination of the particles. Agglutination is detected and the presence of agglutination indicates the presence of the target polynucleotide sequence.

Another method in accordance with the present invention for detecting a target polynucleotide sequence comprises combining a sample suspected of containing the target polynucleotide sequence with two probes capable of binding to the same strand of the target polynucleotide sequence wherein each of the probes is bound to or capable of binding to a particle and detecting the target polynucleotide sequence by detecting the association of the particles. At least one of the probes has two sequences that are non-contiguous and can bind to contiguous or noncontiguous sites on a single strand of the target polynucleotide sequence.

Another aspect of the present invention is a reagent for detecting a target polynucleotide sequence. The reagent comprises two oligonucleotide probes capable of binding to a single strand of the sequence wherein one of the probes has two that either (i) are non-contiguous and can bind to contiguous or non-contiguous sites on a single strand of the target polynucleotide sequence or (ii) can bind to noncontiguous sites on a single strand of the targ et polynucleotide sequence.

BRIEF DESCRIPTION OF THE DRAWINGS

FIGS. 1–11 are schematic diagrams depicting alternate embodiments in accordance with the present invention.

DESCRIPTION OF THE SPECIFIC EMBODIMENTS

The present invention provides for detection of nucleic acid sequences, particularly, the products of nucleic acid amplification reactions that require the use of elevated temperatures. All of the necessary reagents for amplification and detection may be included in the reaction mixture prior to amplification and it is not necessary to open the reaction vessel and/or to separate reagents and products after amplification and prior to binding of probes, which binding is subsequently subjected to detection. Thus, contamination is avoided.

The invention relates to the use of two or more probes for the detection of a target polynucleotide sequence. Preferably, a pair of probes is used wherein at least one of the probes is a looped probe. However, two or more linear probes, usually two linear probes may be employed where at least one of the probes is bound to or is capable of becoming bound to a particle. The two probes are able to bind to a single strand of the target polynucleotide and one, preferably both, of the probes are comprised of a label. The looped probes have two polynucleotide sequences that are non-contiguous and/or bind to non-contiguous sequences within the target polynucleotide sequence. This property is especially useful for detection of the products of nucleic acid amplification. When an amplification is carried out at temperatures that exceed the melting temperature of the looped probe with the amplicon (the temperature where the amplicon and looped probe dissociate), the probe can be combined with the amplification reagents and yet not interfere with the amplification. In the case of amplification employing primer extension, a primer may be employed that permits the introduction, into the product of the amplification, of one member of specific binding pair such as biotin. In this latter situation only one looped probe may be used in conjunction with a labeled recognition sequence that binds to the looped probe and a labeled other member of the specific binding pair such as avidin. Preferably, association of the labels in the final product is detected.

In its broadest aspect the present invention relates to a method for detecting a target polynucleotide sequence. More particularly, the present invention relates to a method for amplifying and detecting a target polynucleotide sequence. The method comprises combining all reagents for conducting an amplification and detection of a target polynucleotide sequence in a single reaction container, amplifying the target polynucleotide sequence to form copies thereof, and detecting the copies. The presence of such copies indicates the presence of the target polynucleotide sequence. Included with the above reagents are two oligonucleotide probes that are capable of hybridizing to the target polynucleotide sequence or copies thereof produced during the amplification. These probes do not interfere in the amplification of the target polynucleotide sequence. The oligonucleotide probes optionally may be linked together by a bond or a linking group comprised of nucleotides or nucleotide analogs. Alternatively, or in conjunction therewith, one of the reagents is a suspendable particle and there is no subsequent segregation or separation of the particles from the reaction medium. The particle may serve as a label on one of the oligonucleotide probes.

In one aspect the present invention relates to a method for detecting a target polynucleotide sequence comprising combining the target polynucleotide with two oligonucleotide probes capable of binding to the target polynucleotide wherein at least one of the probes has two sequences that either (i) are non-contiguous and bind to contiguous or non-contiguous sites on a single strand of the target polynucleotide sequence or (ii) are contiguous and can bind to non-contiguous sites on a single strand of the target polynucleotide sequence.

In another aspect the present invention relates to a method for amplifying and detecting a target polynucleotide sequence. The method comprises providing in combination (i) a medium suspected of containing the target polynucleotide sequence, (ii) all reagents required for conducting an amplification of the target polynucleotide sequence, and (iii) two oligonucleotide probes capable of binding to a single strand of the product of the amplification. At least one of the probes has two sequences that either (i) are non-contiguous and can bind to contiguous or noncontiguous sites on the single strand or (ii) are contiguous and can bind to noncontiguous sites on the single strand. Each probe may contain a label. The combination is subjected to conditions for amplifying the target polynucleotide sequence. Next, and without separation the combination is subjected to conditions under which both of the probes hybridize to one of the strands to form a termolecular complex. Detection of the termolecular complexes is carried out by means of the label and additional members of the signal producing system may be added at this time, if necessary.

Before proceeding further with a description of the specific embodiments of the present invention, a number of terms will be defined.

Polynucleotide analyte—a compound or composition to be measured that is a polymeric nucleotide, which in the intact natural state can have about 20 to 5,000,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids, and fragments thereof, from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide analyte can be only a minor fraction of a complex mixture such as a biological sample. The analyte can be obtained from various biological material by procedures well known in the art. Some examples of such biological material by way of illustration and not limitation are disclosed in the following Table:

TABLE

Microorganisms of interest include:

Corynebacteria
*Corynebacterium diphtheria*
Pneumococci
*Diplococcus pneumoniae*
Streptococci
*Streptococcus pyrogenes*
*Streptococcus salivarus*
Staphylococci
*Staphylococcus aureus*
*Staphylococcus albus*

TABLE-continued

Microorganisms of interest include:

| | |
|---|---|
| Neisseria | |
| *Neisseria meningitidis* | |
| *Neisseria gonorrhea* | |
| Enterobacteriaciae | |
| *Escherichia coli* | |
| *Aerobacter aerogenes* | The colliform |
| *Klebsiella pneumoniae* | bacteria |
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| *Hemophilus influenza, H. ducryi* | *Rhizopus arrhizua* Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | *Poxvirus bovis* |
| *Mycobacterium leprae* | Paravaccinia |
| *Mycobacterium paratuberculosis* | *Molluscum contagiosum* |
| Actinomycetes (fungus-like bacteria) | Picornaviruses |
| *Actinomyces lsaeli* | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza(A, B, and C) |
| *Treponema pallidum Spirillum minus* | Parainfluenza (1–4) |
| *Treponema pertenue Streptobacillus monoiliformis* | Mumps Virus |
| | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Eucephalitis Virus |

TABLE-continued

Microorganisms of interest include:

| | |
|---|---|
| *Listeria monocytogenes* | Western Equine Eucephalitis Virus |
| *Erysipelothrix rhusiopathiae* | Sindbis Virus |
| *Streptobacillus monoiliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| *Mucor corymbifer* (*Absidia corymbifera*) | |

Also included are genes, such as hemoglobin gene for sickle-cell anemia, cystic fibrosis gene, oncogenes, cDNA, and the like.

The polynucleotide analyte, where appropriate, may be cleaved to obtain a fragment that contains a target polynucleotide sequence, for example, by shearing or by treatment with a restriction endonuclease or other site specific chemical cleavage method.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90–100° C. for a period of about 1 to 10 minutes to produce denatured material.

Amplification of nucleic acids or polynucleotides—any method that results in the formation of one or more copies of a nucleic acid or polynucleotide molecule (exponential amplification) or in the formation of one or more copies of only the complement of a nucleic acid or polynucleotide molecule (linear amplification).

Exponential amplification of nucleic acids or polynucleotides—any method that results in the formation of one or more copies of a nucleic acid or polynucleotide molecule present in a medium. The amplification products are sometimes referred to as "amplicons." One such method for the enzymatic amplification of specific double stranded sequences of DNA is known as the polymerase chain reaction (PCR), as described above. This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is mentioned above and involves amplification of a single stranded polynucleotide using a single oligonucleotide primer. The single stranded polynucleotide that is to be amplified contains two noncontiguous sequences that are complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving a nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid.

Another method for amplifying a specific group of nucleic acids is the Q-beta-replicase method, which relies on the ability of Q-beta-replicase to amplify its RNA substrate exponentially.

Linear amplification of nucleic acids or polynucleotides—any method that results in the formation of one or more copies of the complement of only one strand of a nucleic acid or polynucleotide molecule, usually a nucleic acid or polynucleotide analyte, present in a medium. Thus, one difference between linear amplification and exponential amplification is that the latter produces copies of both strands of a nucleic acid whereas the former produces only the complementary strand of a polynucleotide. In linear amplification the number of complements formed increases as a linear function of time as opposed to exponential amplification where the number of copies is an exponential function of time.

Target sequence of a target polynucleotide—a sequence of nucleotides to be identified, usually existing within a portion (target polynucleotide) or all of a polynucleotide analyte, the identity of which is known to an extent sufficient to allow preparation of various primers and other molecules necessary for conducting an amplification of the target sequence contained within the target polynucleotide. In general, in primer extension amplification primers hybridize to, and are extended along (chain extended), at least the target sequence within the target polynucleotide and, thus, the target sequence acts as a template. The extended primers are chain "extension products." The target sequence usually lies between two defined sequences but need not. In general, the primers hybridize with the defined sequences or with at least a portion of such target polynucleotide, usually at least a ten nucleotide segment at the 3'-end thereof and preferably at least 15, frequently 20 to 50 nucleotide segment thereof. The target sequence usually contains from about 30 to 5,000 or more nucleotides, preferably 50 to 1,000 nucleotides. The target polynucleotide is generally a fraction of a larger molecule or it may be substantially the entire molecule (polynucleotide analyte). The minimum number of nucleotides in the target polynucleotide sequence is selected to assure that the presence of target polynucleotide in a sample is a specific indicator of the presence of polynucleotide analyte in a sample. Very roughly, the sequence length is usually greater than about 1.6 log L nucleotides where L is the number of base pairs in the genome of the biologic source of the sample. The maximum number of nucleotides in the target polynucleotide is normally governed by the length of the polynucleotide analyte and its tendency to be broken by shearing, or other processes during isolation and any procedures required to prepare the sample for assay and the efficiency of detection and/or amplification of the sequence.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 10 to 100 nucleotides, more preferably, 20 to 50 nucleotides, and usually 10 to 30 nucleotides in length.

Various techniques can be employed for preparing an oligonucleotide utilized in the present invention. Such oligonucleotide can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol,* 101, 20–78.

Other methods of oligonucleotide synthesis include phosphotriester and phosphodiester methods (Narang, et al. (1979) *Meth. Enzymol* 68: 90) and synthesis on a support (Beaucage, et al. (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Oligonucleotide probe—an oligonucleotide employed in the present invention to bind to a portion of a target polynucleotide sequence. The design and preparation of the oligonucleotide probes are important in performing the methods of this invention. One consideration is that the oligonucleotide probe does not substantially hybridize to the copies of the target polynucleotide sequence during the amplification in which such copies are produced. Furthermore, after the amplifying step both of the oligonucleotides do hybridize to one of the strands of the copies provided such copies are produced. This is related to the presence or absence of the target polynucleotide sequence in a target polynucleotide suspected of being in a sample. A more detailed description of oligonucleotide probes in accordance with the present invention is found hereinbelow.

Oligonucleotide primer(s)—an oligonucleotide that is usually employed in a chain extension on a polynucleotide template such as in, for example, an amplification of a nucleic acid. The oligonucleotide primer is usually a synthetic nucleotide that is single stranded, containing a sequence at its 3'-end that is capable of hybridizing with a defined sequence of the target polynucleotide. Normally, an oligonucleotide primer has at least 80%, preferably 90%, more preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the oligonucleotide primer will be at least as great as the defined sequence of the target polynucleotide, namely, at least ten nucleotides, preferably at least 15 nucleotides and generally from about 10 to 200, preferably 20 to 50, nucleotides.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates. Examples of such derivatives or analogs, by way of illustration and not limitation, are those which are biotinylated, amine modified, alkylated, and the like and also include phosphorothioate, phosphite, ring atom modified derivatives, and the like.

Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during an amplification reaction and therefore becoming part of the nucleic acid polymer.

Nucleoside—is a base-sugar combination or a nucleotide lacking a phosphate moiety.

Nucleotide polymerase—a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (1, 11, or 11), T4 DNA polymerase, T7 DNA polymerase, Klenow fragment, reverse transcriptase, Vent DNA polymerase, Pfu DNA polymerase, Taq DNA polymerase, and the like, derived from any source such as cells, bacteria, such as E. coli, plants, animals, virus, thermophilic bacteria, and so forth.

Wholly or partially sequentially—when the sample and various agents utilized in the present invention are combined other than concomitantly (simultaneously), one or more may be combined with one or more of the remaining agents to form a subcombination. Subcombination and remaining agents can then be combined and can be subjected to the present method.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical polynucleotides— In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Non-contiguous—two sequences within a single polynucleotide sequence are non-contiguous when the nucleotides at the ends joining the two sequences do not hybridize with adjacent nucleotides of a complementary polynucleotide sequence upon hybridization of the single polynucleotide strand with the complementary polynucleotide sequence. Normally, the nucleotides at the ends are connected by a chain of greater or less than 10 atoms or are attached to the ends of a 10-atom chain in a manner in which they cannot simultaneously bind to adjacent nucleotides on a complementary polynucleotide strand. Conveniently, non-contiguous sequences are connected by one or more nucleotide phosphates that are not bound to a complementary polynucleotide sequence when the non-contiguous sequences are bound. Alternatively, the sequences may be connected by hydroxyalkyl phosphates other than a nucleoside monophosphate. The exact nature of the chain linking the two sequences can vary widely and may contain a wide variety of groups as, for example, alkylenes, ethers, esters, sulphones, sulphates, aralkyls, carboxaines, sulphonamides, phosphonates, carbamates and the like.

Contiguous—two sequences within a single polynucleitde strand are contiguous when the nucleotides at the ends joining the two sequences hybridizes with adjacent nucleotides of a complementary polynucleotide sequence when the single polynucleotide strand hybridizes with the complementary polynucleotide sequence. Probes containing only contiguous sequences are called linear probes.

Copy of a sequence—a sequence that is a direct identical copy of a single stranded polynucleotide sequence as differentiated from a sequence that is complementary to the sequence of such single stranded polynucleotide.

Means for extending a primer—a nucleotide polymerase or a single stranded template polynucleotide having a sequence other than at its 3'-end that can hybridize to at least the 3'-end of the primer or both. Means for extending a primer also includes nucleoside triphosphates or analogs thereof capable of acting as substrates for the enzyme and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label—a member of a signal producing system. Usually the label is part of an oligonucleotide probe either being conjugated thereto or otherwise bound thereto or associated therewith and is capable of being detected directly or indirectly. The label may be part of the oligonucleotide primer. Labels include reporter molecules that can be detected directly by virtue of generating a signal, specific binding pair members that may be detected indirectly by subsequent binding to a cognate that contains a reporter molecule, oligonucleotide primers that can provide a template for amplification or ligation or a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used. The reporter molecule can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label is a member of a signal producing system and can generate a detectable signal either alone or together with other members of the signal producing system. As mentioned above, a reporter molecule can be bound directly to a nucleotide sequence or can become bound thereto by being bound to an sbp member complementary to an sbp member that is bound to a nucleotide sequence. Examples of particular labels or reporter molecules and their detection can be found in U.S. patent application Ser. No. 07/555,323 filed Jul. 19, 1990, the relevant disclosure of which is incorporated herein by reference.

Signal Producing System—the signal producing system may have one or more components, at least one component being the label. The signal producing system generates a signal that relates to the presence or amount of target polynucleotide sequence or a polynucleotide analyte in a sample. The signal producing system includes all of the reagents required to produce a measurable signal. When a reporter molecule is not conjugated to a nucleotide sequence, the reporter molecule is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances; and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in U.S. patent application Ser. No. 07/555,323, filed Jul. 19, 1990, the relevant disclosure of which is incorporated herein by reference.

Termolecular complex—a complex formed in accordance with the present methods upon the binding of two oligonucleotide probes to a single strand of the product of an amplification of a target polynucleotide sequence. Such complex is termolecular in that it involves three molecules, namely, the two oligonucleotide probes and the single strand of such amplification product.

Ancillary Materials—Various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above one aspect of the present invention provides for detection of a target polynucleotide sequence such as, for example, the products of nucleic acid amplification reactions that require the use of elevated temperatures. When an amplification is employed, all of the necessary reagents for amplification and detection may be included in the reaction mixture prior to amplification and it is not necessary to open the reaction vessel after amplification and prior to detection. Thus, contamination is avoided. At the very least, complexes containing labels can be formed after amplification and without a separation step or opening of the reaction container, and then remaining members of the signal producing may be added, if necessary.

The combination of reagents in a single reaction container, if desired, is subjected to conditions for amplifying the target polynucleotide sequence to form copies thereof. The reagents comprise at least two polynucleotide probes that hybridize with the copies only after the amplification and are not substantially incorporated into the copies during the amplification. At least one of the probes has at least two non-contiguous sequences. Additionally, at least one of the probes comprises a label. The copies are then detected by means of the binding of both probes to a single strand of the amplification product. The presence of the copies indicates the presence of the target polynucleotide sequence.

As mentioned above, two oligonucleotide probes capable of binding to a single strand of the product of an amplification reaction ("amplicon") are employed in the methods of the present invention. At least one of such probes is "looped" in that it has two sequences (the "recognition sequences") that bind to two sequences of the amplicon (the "target sequences") wherein the recognition sequences are either (i) non-contiguous and bind to contiguous or non-contiguous sites on the target polynucleotide sequences or (ii) contiguous and bind to non-contiguous sites on the target polynucleotide sequences. The other of such oligonucleotide probes may be linear or looped.

When the amplification uses a DNA polymerase, preferably, both of the oligonucleotide probes are blocked at the 3'-end to avoid any potential interference with and during amplification. To this end, the 3'-end of the recognition sequences can be blocked by a group that cannot undergo chain extension, such as, for example, an unnatural group such as a 3'-phosphate, a 3'-terminal dideoxy, an abasic ribophosphate, a polymer or surface, or other means for inhibiting chain extension. Alternatively, a polynucleotide that does not hybridize to the amplicon is attached to the 3'-end. Such an end group can be introduced at the 3' end during solid phase synthesis or a group can be introduced that can subsequently be modified. For example, in order to introduce dextran at the 3'-end a ribonucleotide can be introduced at the 3'-end and then oxidized with periodate followed by reductive amination of the resulting dialdehyde with borohydride and aminodextran. The details for carrying out the above modifications are well-known in the art and will not be repeated here.

Examples of desirable characteristics of oligonucleotide probes in accordance with the invention are set forth in FIGS. 1–5, by way of example and not limitation. One embodiment of an oligonucleotide probe in accordance with the present invention is shown in FIG. 1. In this embodiment oligonucleotide probe OP1 has recognition sequences S1 and S2 wherein the distal ends of S1 and S2 are linked, that is, the 3'-end of S2 is linked by means of L1 to the 5'-end of S1 (also referred to herein as "knot probe"). S1 and S2 bind to a single strand of the amplicon in such a manner that the 3'-end of S1 is contiguous with the 5'-end of S2. In this embodiment the recognition sequences bind to contiguous sites on a single strand of the amplicon containing TS1.

Sequences S1 and S2 are recognition sequences in that they bind to different sites on a single strand of an amplicon. The recognition sequences are relatively short, usually about 8 to 25 nucleotides in length, preferably, 10 to 20 nucleotides in length. S1 and S2 are linked by, and therefore separated from one another by a group L1, which does not bind to TS1. L1 may be a sequence of nucleotides that may include one or more modified nucleotides. Alternatively, L1 can contain polyethyleneglycols, polyalkylidene phosphates, polypeptides, and the like. L1 may be a bond as shown in FIG. 5. In the embodiments depicted in FIGS. 1–4, such linking group is usually a chain of at least 6 to 300 or more atoms, preferably, between 20 to 180 atoms. Usually, it is convenient to attach the 5'-end of the linking group to the 3'-end of one of the recognition sequences and the 3'-end thereof to the 5'-end of the other. However, it is not necessary to attach the linking group to the ends of the recognition sequences. The main function of the group L1 is to link the two recognition sequences together.

The design of the oligonucleotide probes used in the present invention as described above permits a high level of recognition of the amplification product because both recognition sequences are involved in binding to a single strand of such product. In addition, the recognition sequences bind to the single strand at only relatively low temperature and, therefore do not interfere with amplification processes, which are usually carried out at elevated temperatures. In the case of linear oligonucleotide probes, i.e., probes with only one recognition sequence binding to one complementary sequence, the length is relatively short, usually, less that 25 oligonucleotides, to avoid binding at higher temperatures and interference with amplification. As described above, a linear probe is usually blocked at its 3'-end to prevent chain extension of the linear probe when used in an amplification procedure that employs a DNA polymerase. The linear probe can be composed of a sequence that hybridizes to the target polynucleotide sequence and a sequence that serves as a label. The latter sequence may be at the 5' or the 3' end of the linear probe.

Another embodiment of an oligonucleotide probe in accordance with the present invention is shown in FIG. 2. In this embodiment oligonucleotide probe OP2 is has recognition sequences S'1 and S'2 wherein the distal ends of S'1 and S'2 are linked, that is, the 5'-end of S'1 is linked by means of L2 to the 3'-end of S'2. S'1 and S'2 bind to a single strand of the amplicon having a target polynucleotide sequence consisting of TS2 and TS'2, which correspond to the binding sites of S'1 and S'2, respectively. As can be seen, TS2 and TS'2 are separated by a sequence LP1, which does not hybridize to OP2. In this embodiment the recognition sequences bind to non-contiguous sites on a single strand of the amplicon.

Another embodiment of the present invention is depicted in FIG. 3, where oligonucleotide probe OP3 has two sequences S1 and S2 that are not contiguous with one another. In the embodiment of FIG. 3 the proximal ends of S1 and S2 are linked together, that is, the 5'-end of S2 and the 3'-end of S1 are connected by L3. The recognition sequences bind to contiguous sites on a single strand of the amplicon containing TS1.

Another embodiment of an oligonucleotide probe in accordance with the present invention is shown in FIG. 4. In this embodiment oligonucleotide probe OP4 has recognition sequences S'1 and S'2 wherein the proximal ends of S'1 and S'2 are linked, that is, the 5'-end of S'2 is linked by means of L4 to the 3'-end of S'1. S'1 and S'2 bind to a single strand of the amplicon having a target polynucleotide sequence consisting of TS2 and TS'2, which correspond S'1 and S'2, respectively. As can be seen, TS2 and TS'2 are separated by a sequence LP1, which does not hybridize to OP4. In this embodiment the recognition sequences bind to non-contiguous sites on a single strand of the amplicon.

Another embodiment of an oligonucleotide probe in accordance with the present invention is shown in FIG. 5. In this embodiment oligonucleotide probe OP5 has a recognition sequence S, which, although linear, binds to a single strand of an amplicon having a target polynucleotide sequence consisting of TS3 and TS'3, which correspond to the entire sequence S. As can be seen, TS3 and TS'3 are separated by a sequence LP2, which does not hybridize to OP5. In this embodiment OP5 binds to non-contiguous sites on a single strand of the amplicon, which sites are rendered contiguous by virtue of the binding of OP5, which in turn is based on the nucleotide composition of S relative to TS3 and TS'3.

As mentioned above, in the present invention two oligonucleotide probes are used to bind to a single strand of an amplicon. Various embodiments of this aspect of the present invention are depicted in FIGS. 6–9, by way of illustration only and not as a limitation. One skilled in the art will appreciate that many combinations of oligonucleotide probes may be used in accordance with the teaching contained herein. In the embodiment depicted in FIG. 6, OP1 (FIG. 1) is used in conjunction with a linear oligonucleotide probe (LOP1). OP1 binds to a portion PTS1 of a single strand of the amplicon of the target polynucleotide sequence TS and LOP1 binds to portion PTS2 of such single strand containing TS other than the portion to which OP1 binds. As depicted in FIG. 6, PTS2 lies 5' of PTS1, but the relative position of the binding of the two oligonucleotide probes is arbitrary. Generally, the two binding sites on a single strand containing the target polynucleotide sequence are separated by 0 to 2000 nucleotides from one another, preferably 20 to 1000 nucleotides.

In another embodiment as depicted in FIG. 7, the two oligonucleotide probes employed are OP1 (FIG. 1) and OP3 (FIG. 3). OP1 binds to portion PTS1 of a single strand containing TS and OP3 binds to portion PTS2' of the same single strand containing TS.

FIG. 8 depicts another embodiment in accordance with the present invention wherein OP1 and OP4 (FIG. 4) are employed as the oligonucleotide probes. OP1 hybridizes with PTS1 and OP3 hybridizes with PTS2", where PTS1 and PTS2" are within the same single strand of the amplicon containing TS.

Another example of an embodiment in accordance with the present invention is shown in FIG. 9. OP4 (FIG. 4), which binds to PTS1' of the single strand containing TS, and OP5 (FIG. 5), which binds to PTS2" of the same single strand of amplicon containing TS, are used as the two oligonucleotide probes in accordance with the present invention.

An example of an embodiment of an amplification, by way of illustration and not limitation, in accordance with the present invention is depicted in FIG. 10. The invention has application to other methods mentioned above for amplification of nucleic acids. The amplification method shown in FIG. 10 (ASPP) is one described above using a single oligonucleotide primer (U.S. patent application Ser. Nos. 07/299,282 and 07/399,795, filed Jan. 19, 1989, and Aug. 29, 1989, and U.S. patent application Ser. No. 08/140,369 filed Oct. 20,1993, the relevant disclosures of which is incorporated herein by reference)). In the embodiment shown in FIG. 10, a sample suspected of containing a target polynucleotide sequence TS is combined in an appropriate medium with oligonucleotide primer PP1, the four common nucleoside triphosphates (NTP's), a nucleotide polymerase (NP), OP1 and OP3. The combination is first treated under conditions for amplifying TS. To that end the combination is subjected to temperature cycling. Normally, in conducting an ASPP amplification the medium is cycled between two or three temperatures. The temperatures for the amplification methods generally range from about 60 to 99° C., more usually from about 60 to 95° C. The exact temperatures can be varied depending on the salt concentration, pH, solvents used, length of and composition of the target polynucleotide sequence and the oligonucleotide primer. Relatively low temperatures of from about 60 to 75° C. can be employed for the extension steps, while denaturation and hybridization can be carried out at a temperature of from about 80 to 99° C. In the amplification PP1 binds to TS and is extended along TS to produce a strand (EPP1) that is complementary to TS. Subsequent denaturation, hybridization and extension occurring as a result of the temperature cycling yield strands that are both the complement (EPP1) and the copy (EPP2) of TS as can be seen in FIG. 10.

In carrying out an amplification as part of the present method, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8. In general for amplification, the pH and temperature are chosen and varied, as the case may be, so as to cause, either simultaneously or sequentially, dissociation of any internally hybridized sequences, hybridization of the oligonucleotide primer with the target polynucleotide sequence, extension of the primer, and dissociation of the extended primer. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

The amplification is conducted for a time sufficient to produce the desired number of copies of the target polynucleotide sequence. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 5 to 80, frequently 10–60. As a matter of convenience it is usually desirable to minimize the time period and the number of cycles. In general, the time period for a given degree of amplification can be shortened, for example, by reducing the volume of the reaction mixture and the heat capacity of the reaction vessel. Generally, the time period for conducting the entire method will be from about 20 to 200 minutes. As a matter of convenience, it will usually be desirable to minimize the time period.

The concentration of the nucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The amount of the target polynucleotide sequence which is to be copied can be as low as one or two molecules in a sample but generally may vary from about 10 to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M. The amount of the oligonucleotide primer(s) will be at least as great as the number of copies desired and will usually be $10^{-13}$ to $10^{-8}$ moles per sample, where the sample is 1–1,000 mL. Usually, the primer(s) are present in at least $10^{-9}$ M, preferably $10^{-7}$ M, and more preferably at least about $10^{-6}$ M. Preferably, the concentration of the oligonucleotide primer(s) is substantially in excess over, preferably at least 100 times greater than, more preferably, at least 1000 times greater than, the concentration of the target polynucleotide sequence. The concentration of the nucleoside triphosphates in the medium can vary widely; preferably, these reagents are present in an excess amount. The nucleoside triphosphates are usually present in $10^{-6}$ to $10^{-2}$M, preferably $10^{-5}$ to $10^{-3}$M.

The order of combining of the various reagents to form the combination may vary. When no amplification is used the target polynucleotide sequence is combined with the oligonucleotide probes. Usually, the mixture is heated to denature the target and the temperature is there adjusted to permit binding of the probes with the target. When amplification using a DNA polymerases is required, generally, the target polynucleotide sequence is obtained from a sample containing such sequence or a polynucleotide analyte that has been treated to obtain such sequence. Generally, the target polynucleotide sequence is combined with a preprepared combination of nucleoside triphosphates and nucleotide polymerase. The oligonucleotide primer(s) and the oligonucleotide probes may be included in the prepared combination or may be added subsequently. However, simultaneous addition of all of the above, as well as other step-wise or sequential orders of addition, may be employed provided that all of the reagents described above are combined prior to the start of the amplification.

Generally, it is desirable to increase the number of copies of the extended primer by at least a factor of $10^2$, preferably a factor of $10^4$, more preferably $10^6$ or more.

The medium is next examined to determine the presence of the target polynucleoitide sequence. In accordance with the present invention the two oligonucleotide probes, OP1 and OP3 in FIG. 10, which are already present in the reaction medium, are used for the determination. To this end the reaction medium is subjected to conditions to allow for the binding of both oligonucleotide probes to the same strand of the amplicon EPP2. Usually, merely lowering the temperature of the reaction medium will permit the oligo-nucleotide probes to bind to the amplicon because of the design of the oligonucleotide probes. The temperature chosen is dependent on the structure of the oligonucleotide probes and the nucleotide sequence of the amplicon. In general, the temperature for this aspect of the present invention is below 55° C., preferably, 35° to 50° C. The structure of the probes and the amplicon affect the choice of temperature which is determined empirically. In general, shorter recognition sequences permit lower temperatures to be used for hybridization. The use of relatively high concentrations of the oligonucleotide probes assists in achieving hybridization of the probes with the target polynucleotide sequence during the detection part of the present method rather than the competing hybridization of the target with its complementary strand and, where DNA polymerase is present, with chain extension of oligonucleotide primer along the amplicon. However, too high concentration of the oligonucleotide probes can result in interference with detection of the probes by producing excess unmodulatable signal or saturating binding substances designed to capture bound probe. An optimum concentration must, therefore, be chosen that balances the effect of competitive target rehybridization and primer chain extension when relatively low concentrations of probe are used with the less efficient detection at high probe concentrations. Such an optimum concentration is usually determined empirically. In general, the concentration of the oligonucleotide probes can vary considerably, usually being in the range of 0.01 nM to 10 $\mu$M, preferably, 1 nM to 100 nM.

It is also within the scope of the present invention to achieve more effective competition of the binding of the oligonucleotide probes with chain extension by assuring that the sequence on the amplicon that is complementary to the probe is relatively remote from the primer binding site, usually at least 50, preferably at least 80, more preferably, at least 150 nucleotides. Additionally, competition with rehybridization of the two target polynucleotide sequence strands can be minimized by optimizing the length of the linker in a looped probe to increase the rate of the binding of the oligonucleotide probes to the amplicon. Again, the optimization in this aspect of the present invention is carried out empirically. Where chain extension may compete with binding of the oligonucleotide probes during this part of the method, it is preferred, although not necessary, to employ oligonucleotide probes of the knot type as exemplified in FIGS. 1 and 2, above, to bind to a site on the target sequence that is 3' of the binding site of the other of the oligonucleotide probes used in the present method. In such a situation the other probe may be any probe of the type exemplified in FIGS. 1–5, above.

Detection of the two oligonucleotide probes hybridized to a single strand of the target polynucleotide sequence is accomplished by using at least one label for each probe. Generally, each probe contains at least one label that facilitates detection of the probes hybridized to a single strand of the target polynucleotide sequence. The labels and other reagents of the signal producing system must be stable at the elevated temperatures used in the amplification of target polynucleotide sequence. Detection of the signal will depend upon the nature of the signal producing system utilized. If the reporter molecule is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

In one aspect of the present invention detection of the binding of the oligonucleotide probes to the single strand of the target polynucleotide sequence is accomplished by employing at least one suspendable particle, which may be a detectable reporter molecule bound directly to a probe or may be bound to an sbp member that is complementary to an sbp member attached to a probe. Such a particle serves as a means of segregating the bound target polynucleotide sequence from the bulk solution, for example, by settling, electrophoretic separation or magnetic separation. A labeled second probe or a label that becomes integrated into the amplicon during amplification is a part of the signal producing system that is separated or concentrated in a small region of the solution to facilitate detection. Typical labels that may be used in this particular embodiment are fluorescent labels, particles containing a photosensitizer and a chemiluminescent olefin (see U.S. Ser. No. 07/923,069 filed Jul. 31, 1992, the disclosure of which is incorporated herein by reference) and electroluminescent labels.

Preferably, the particle itself can serve as part of a signal producing system that can function without separation or segregation. For example, the determination can be accomplished by bead agglutination that is detected by fluorescence. In another approach, the second probe or the amplicon can carry a second label that is also part of the signal producing system and that can produce a signal in concert with the particle to provide a homogeneous assay detection method. A variety of combinations of labels can be used for this purpose with the limitation that the labels must be stable to the elevated temperatures when temperature cycling is used for amplification. Thus, for example, the particle may be a simple latex particle or it may be a particle comprising a photosensitizer, chemiluminescer, fluorescer, dye, and the like. The second label must be or be capable of binding to a member of the signal producing system that interacts with the particle when bound to it to produce or modulate a signal. Typical particle/label pairs include: (1) a dye crystallite and a fluorescent label where binding causes fluorescence quenching, (2) two latex particles, the association of which is detected by light scattering or turbidimetry, (3) one particle capable of absorbing light and a second label particle which fluoresces upon accepting energy from the first, and (4) a particle incorporating a photosensitizer and a label particle incorporating a chemiluminescer as described for the induced luminescence immunoassay referred to in U.S. Ser. No. 07/704,569, filed May 22, 1991, entitled "Assay Method Utilizing Induced Luminescence", which disclosure is incorporated herein by reference.

In each of the above approaches no chemical reagent need be added to the mixture following amplification.

Briefly, detection using the induced luminescence assay as applied in the present invention involves employing a photosensitizer as part of one label and a chemiluminescent compound as part of the other label. If the target is present the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed. By way of illustration as applied to the present invention a particle is employed, which comprises the chemiluminescent compound associated therewith such as by incorporation therein or attachment thereto. The particles have a nucleotide sequence attached thereto with a complementary sequence incorporated into one of the oligonucleotide probes of the present invention usually in the linking group linking the two recognition sequences of such probe. Another particle is employed that has the photosensitizer associated therewith. These particles have a nucleotide sequence attached thereto, which is different than that attached to the chemiluminescent particles. A complementary sequence is incorporated in the other of the probes of the present invention. Once the medium has been treated in accordance with the present invention to form a termolecular complex and to allow the particles to bind to the probes by virtue of the complementary nucleotide sequences on the probes and the particles, the medium is irradiated with light to excite the photosensitizer, which is capable in its excited state of activating oxygen to a singlet state. Because the chemiluminescent compound of one of the sets of particles is now in closes proximity to the photosensitizer by virtue of the presence of the target polynucleotide, it is activated by the singlet oxygen and emits luminescence. The medium is then examined for the presence and/or the amount of luminescence or light emitted, the presence thereof being related to the presence of the termolecular complex. The presence of the latter indicates the presence and/or amount of the target polynucleotide.

Another embodiment of the present invention is depicted in FIG. 11. In this embodiment an amplification by PCR is chosen by way of example and not limitation. The sample suspected of containing the nucleic acid or target polynucleotide having a target polynucleotide sequence complementary strands (TS1 and TS2 for the double stranded polynucleotide analyte) to be amplified by PCR is combined with two different oligonucleotide primers (OPP1 and OPP2), a nucleotide polymerase (NP), nucleoside triphosphates (NTP's) and two oligonucleotide probes (OP1 and OP4). The combination is first treated under conditions for amplifying TS1 and TS2. To that end the combination is subjected to temperature cycling. Normally, in conducting amplification by PCR the medium is cycled between two or three temperatures to achieve denaturing, hybridization of primers to the denatured strands, and extension of primers along the strands. The temperatures for the PCR amplification generally range from about 60 to 99° C., more usually from about 60 to 95° C., as more fully described above for temperature cycling. In the amplification OPP1 and OPP2 bind to their respective strands TS1 and TS2 and are extended along TS1 and TS2 to produce multiple copies of TS. Molecules EOPP1 and EOPP2 serve as templates for primers OPP2 and OPP1, respectively.

Once the desired member of copies have been generated, the medium is examined to determine the presence of amplicons. In accordance with the present invention the two oligonucleotide probes, OP1 and OP4 in FIG. 11, which are already present in the reaction medium, are used for the determination. To this end the reaction medium is subjected to conditions to allow for the binding of the two oligonucleotide probes both to the same strand of TS, either TS1 and TS2. Accordingly, multiple strands of TS2, for example, each have OP1 and OP4 bound to each strand at PTS'1 and PTS'3, respectively. As mentioned above, usually, merely lowering the temperature of the reaction medium will permit the oligonucleotide probes to bind to the amplicon. In the embodiment of FIG. 11, OP1 and OP4 each comprise an oligonucleotide label (OL1 and OL2, respectively) in the linker portion L3 and L4, respectively. Oligonucleotide COL1, which is the complement of OL1, and oligonucleotide COL2, which is the complement of OL2, are also included in the amplification mixture either initially or subsequent to the amplification and binding of OP1 and OP4 to TS2. Each of COL1 and COL2 contains a reporter group, L1 and L2, respectively, that produces a signal individually or in concert with one another. Binding of OP1 and OP4 to TS2 is determined by detection of the signal. In one alternate embodiment OP1 is bound to a particle, such as a latex particle, containing a photosensitizer and OP4 is bound to a particle containing a chemiluminescent compound and detection was accomplished using the induced luminescence assay mentioned above. Accordingly, subsequent to hybridization of OP1 and OP4 with TS2 the reaction medium is irradiated and signal is detected. In this manner, the assay for a polynucleotide analyte is conducted homogeneously. The description of photosensitizer and chemiluminescent compound as well as particles, irradiation and light detection are described in U.S. Ser. No. 07/704,569, filed May 22, 1991, for example, at pages 37–80, the disclosure of which is incorporated herein by reference in its entirely.

Where the polynucleotide analyte is RNA, it can be detected by direct binding of the two oligonucleotide , or it can first be converted to DNA by means of a primer and reverse transcriptase, or, as mentioned above, the nucleotide polymerase used can be reverse transcriptase.

In carrying out the method of the invention as applied to the detection of a polynucleotide analyte, the considerations as to media, pH, temperature, and times can be as described above. While the concentrations of the various reagents are generally determined by the concentration range of interest of the polynucleotide analyte, the final concentration of each of the reagents is normally determined empirically to optimize the sensitivity of the assay over the range of interest and provide for reliable control. The concentration of the other reagents in an assay generally is determined following the same principles as set forth above for the amplification method. The primary consideration is that a sufficient number of copies of extended primer(s) be produced in relation to the polynucleotide analyte sequence so that such copies can be readily detected and provide an accurate determination of the polynucleotide analyte.

One aspect of the present invention is a method for detecting at least one double stranded polynucleotide, comprising a single stranded target polynucleotide sequence ("target sequence") and its complementary sequence ("complementary sequence"). A sample suspected of containing one or more of such double stranded polynucleotides is combined in an appropriate medium with oligonucleotide primers capable of hybridizing to a portion of each target sequence and its complementary sequence under conditions for hybridizing the primers to and extending the primers along the target sequence and the complementary sequence. The primers are selected such that the extension product formed from one primer, when it is dissociated from its complement, can serve as a template for the formation of the extension product of another primer thus resulting in an amplifying of the target polynucleotide sequence. Also included in the medium are a nucleotide polymerase, nucleoside triphosphates, a first oligonucleotide probe having nucleotide sequences S1 and S2 wherein the 3'-end of one of S1 and S2 sequences is linked to the 5'-end of the other of the sequences, and a second oligonucleotide probe having sequences S3 and S4 wherein the 3'-end of one of the S3 and S4 sequences is linked to the 5'-end of the other of the sequences. The first and second probes do not hybridize substantially to the target polynucleotide or to the primer extension products during the amplifying and do not interfere substantially with the amplifying. Subsequent to the amplifying the first and second probes do hybridize each to a single strand of a primer extension product. One or both of the probes contain a substituent that facilitates detection of the probes hybridized to the primer extension products. The method comprises dissociating primer extension products from their respective templates to produce single stranded molecules, treating the single stranded molecules produced above with the aforementioned primers under conditions such that a primer extension product is formed using the single strands produced as templates, resulting in amplification of the target sequences and complementary sequences if present. The presence of primer extension products is detected by means of the probes, the presence thereof being related to the presence of the target polynucleotide. In the above method the 3'-end of S1 may be linked to the 5'-end of S2 or the 3'-end of S3 may be linked to the 5'-end of S4. For the detection one of the probes may be associated with a particle and detection comprises detecting agglutination of such particles.

In another embodiment a method of detecting a target sequence of a target polynucleotide comprises providing in combination (1) a single stranded polynucleotide having a sequence that is the target sequence and that is flanked at each end by at least partially complementary first and second flanking sequences, (2) an oligonucleotide primer at least a 10 base portion of which at its 3'-end is hybridizable to that member of the first and second flanking sequences that is at the 3'-end of the single stranded polynucleotide, (3) nucleoside triphosphates, (4) a nucleotide polymerase, (5) a first oligonucleotide probe having nucleotide sequences S1 and S2 wherein the 3'-end of one of the S1 and S2 sequences is linked to the 5'-end of the other of the sequences, and (6) a second oligonucleotide probe having sequences S3 and S4 wherein the 3'-end of one of the S3 and S4 sequences is linked to the 5'-end of the other of the sequences. The combination is incubated under conditions for (1) dissociating the single stranded polynucleotide from any complementary sequences, (2) hybridizing the oligonucleotide primer with the flanking sequence at the 3'-end of the single stranded polynucleotide, (3) extending the oligonucleotide primer along the single stranded polynucleotide to provide a first extended oligonucleotide primer, (4) dissociating the first extended primer and the single stranded polynucleotide, (5) hybridizing the first extended oligonucleotide primer with the oligonucleotide primer, (6) extending the oligonucleotide primer along the first extended oligonucleotide primer to provide a second extended oligonucleotide primer, (7) dissociating the second extended oligonucleotide primer from the first extended oligonucleotide primer, and (8) repeating steps (5)–(7). The first oligonucleotide probe and the second oligonucleotide probe do not interfere with the amplification and preferably do not hybridize to the target sequence or the extended oligonucleotide primer. Subsequent to the amplification, the first and second oligonucleotide probes each hybridize to a single strand of the extended oligonucleotide primer. One or both of the probes contain a substituent that facilitates detection of the probes hybridized to the extended oligonucleotide primer.

The presence of extended oligonucleotide primer is detected by means of the probes, the presence thereof being related to the presence of the target polynucleotide. The probes and conditions may be varied as described above.

As a matter of convenience, predetermined amounts of reagents employed in the present invention can be provided in a kit in packaged combination. A kit can comprise in packaged combination (a) reagents for conducting an amplification of a target polynucleotide sequence comprising at least one oligonucleotide primer capable of binding to such sequence and an enzyme capable of modifying the oligonucleotide primer as a function of the presence of the sequence, (b) two oligonucleotide probes capable of binding to a single strand of the product of amplification wherein at least one the probes has two sequences that either (i) are non-contiguous and can bind to contiguous or non-contiguous sites on the single strand or (ii) can bind to non-contiguous sites on the single strand. At least one probe contains a label, or each probe can contain a label. The kit can also include (c) nucleoside triphosphates and (d) a nucleotide polymerase. The kit can also include a second oligonucleotide primer where the primers are related in that a product of the extension of one along a target sequence serves as a template for the extension of the other. The kit can further include particles capable of binding to the label on each of the probes wherein the labels may be recognition sequences.

The kits above can further include in the packaged combination nucleoside triphosphates such as, e.g., deoxyadenosine triphosphate (dATP), deoxyguanosine triphosphate (dGTP), deoxycytidine triphosphate (dCTP) and deoxythymidine triphosphate (dTTP). The kit can further include members of a signal producing system and also various buffered media, some of which may contain one or more of the above reagents.

A kit for use in an amplification and detection of a target polynucleotide sequence of a target polynucleotide comprises in packaged combination: (a) an oligonucleotide primer which is hybridizable to the target polynucleotide and is extendable along the target polynucleotide sequence to produce extended oligonucleotide primer, (b) nucleoside triphosphates, (c) a nucleotide polymerase, (d) a first oligonucleotide probe having nucleotide sequences S1 and S2, and (e) a second oligonucleotide probe having sequences S3 and S4, wherein the sequences comprising at least one of the first or the second oligonucleotide probes are linked such that they are non-contiguous and/or the sites to which they hybridize on the extended polynucleotide primer or a complementary sequence thereto are noncontiguous and wherein the probes have the characteristics that they (i) do not substantially hybridize to the extended oligonucleotide primer during the amplification and (ii) subsequent to the amplification, both of the first and second oligonucleotide probes can hybridize to the extended oligonucleotide primer or the complementary sequence, and (iii) one or both of the probes contain a label that facilitates detection of the probes hybridized to the extended oligonucleotide primer or the complementary sequence.

Another embodiment of a kit for detection of a target polynucleotide sequence comprises in packaged combination reagents for conducting an amplification of the target polynucleotide sequence and two labeled oligonucleotide probes capable of binding to the product of the amplification of the target polynucleotide sequence. At least one of the probes has two sequences that are non-contiguous and can bind to contiguous or non-contiguous sites on a single strand of the product.

The relative amounts of the various reagents in the kits can be varied widely to provide for concentrations of the reagents which substantially optimize the reactions that need to occur during the present method and to further substantially optimize the sensitivity of the assay and the reliability of the control. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

EXAMPLES

The invention is demonstrated further by the following illustrative examples. Temperatures are in degrees centigrade (°C.) and parts and percentages are by weight, unless otherwise indicated. Unless otherwise indicated, oligonucleotides used in the following examples were prepared by synthesis using an automated synthesizer and were purified by gel electrophoresis or HPLC.

The following abbreviations are used herein:

Tris HCl—Tris(hydroxymethyl)aminomethane-HCl (a 10× solution) from BioWhittaker, Walkersville, Md.

DTT—dithiothreitol from Sigma Chemical Company, St. Louis, Mo.

HPLC—high performance liquid chromatography.

DPP—4,7-diphenylphenanthroline from Aldrich Chemical Company, Milwaukee Wis.

$Eu(TTA)_3$ —europium tri-3-(2-thienoyl)-1,1,1-trifluoroacetonate

BSA—bovine serum albumin from Sigma Chemical Company, St. Louis Mo.

ELISA—enzyme linked immunosorbent assay as described in "Enzyme—Immunoassay," Edward T. Maggio, CRC Press, Inc., Boca Raton, Fla. (1980)

bp—base pairs

POD—peroxidase

Fab fragment—antigen-binding fragment of an antibody ddc—dideoxycytidine g—grams mmol—millimolar DMF—dimethyl formamide THF—tetrahydrofuran LSIMS—fast ion bombardment mass spectroscopy NMR—nuclear magnetic resonance spectroscopy TMSCI—tetramethylsilylchloride EDAC—1-ethyl-3-(3-dimethylaminopropyl)-carbodiimide hydrochloride.

MES—2-(N-morpholino)ethane sulfonic acid.

SPDP—N-succinimidyl 3-(2-pyridylthio)-propionate.

Sulfo-SMCC-4-(N-maleimidomethyl)cyclohexane-1-carboxylate.

TCEP—tris-carboxyethyl phosphine.

Example 1

Homogenous detection of amplification products of E. coli K12 DnaJ gene sequence Various modes of homogeneous detection of amplification of a portion of DnaJ gene sequence from E. coli genome were carried out. The various detection modes employed the novel oligonucleotide probes and photosensitizer and chemiluminescer particles capable of binding to specific labels used.

Chemiluminescer particles having incorporated therein the dye dioctadeconylbenzalacridan and having dT40 oligonucleotide immobilized on their surface The dye dioctadeconylbenzalacridan was prepared and incorporated into latex particles (Seradyn Particle Technology, Indianapolis Ind.) in a manner similar to that described in U.S. Pat. No. 5,340,716 issued Aug. 23, 1994 (the '716 patent), at column 51, lines 3–19, and column 48, lines 24–45, which is incorporated herein by reference. The oligonucleotide dT40 (SEQ ID NO:1) (Oligo Etc., Inc., Oregon) was immobilized on the surface of the above particles in the following manner: Aminodextran (500 mg) was partially maleimidated by reacting it with sulfo-SMCC (157 mg, 10 mL $H_2O$). The sulfo-SMCC was added to a solution of the aminodextran (in 40 mL, 0.05 M $Na_2HPO_4$, pH 7.5) and the resulting mixture was incubated for 1.5 hr. The reaction mixture was then dialyzed against MES/NaCl (2×2L, 10 mM MES, 10 mM NaCl, pH 6.0, 4° C.). The maleimidated dextran was centrifuged at 15,000 rpm for 15 minutes and the supernatant collected. The supernatant dextran solution (54 mL) was then treated with imidazole (7 mL of 1.0 M solution) in MES buffer (pH 6.0) and into this stirred solution was added the stained photosensitizer particles (10 mL of 10 mg/mL). After stirring for 10 minutes the suspension was treated with EDAC (7 mmol in 10 mM pH 6.0 MES) and the suspension stirred for 30 minutes. After this time, SurfactAmps® (Pierce) Tween-20 (10%, 0.780 mL) was added to the reaction mixture for a final concentration of 0.1%. The particles were then centrifuged at 15,000 rpm for 45 minutes and the supernatant discarded. The pellet was resuspended in MES/NaCl (pH 6.0,10 mM, 100 mL) by sonication. Centrifugation at 15,000 rpm for 45 minutes, followed by pellet resuspension after discarding the supernatant, was performed twice. The maleimidated dextran chemiluminescer particles were stored in water as a 10 mg/mL suspension. Amino-dT(40) was prepared on a Milligen Biosearch DNA synthesizer (Model #8750) using standard solid phase phosphoramidite methodology (see Oligonucleotide Syntheses—A Practical Approach (1984), Gait M. J., Ed., IRL Press Oxford.) The protocol briefly consisted of (a) removal with dichloroactic acid of the 5'-dimethoxytrityl group on the nucleoside attached to the solid support; (b) coupling of the incoming nucleoside, which contains a 5'-hydroxyl protecting group (preferably dimethoxytrityl) and a 3'-hydroxyl protecting group (preferably N,N-diisopropylphosphoramidite), using tetrazole as the catalyst; (c) a capping step with acetic anhydride; and (d) iodine oxidation to convert the phosphite triester into a phosphate triester. At the conclusion of the synthesis ammonium hydroxide was used to (a) cleave the synthesized polynucleotide from the support; (b) remove the phosphoryl protecting groups (b-cyanoethyl); and (c) to remove the base protecting groups. Amino-dt(40) (180 mL, 50 nmol) in water was treated with 0.25M borax (50 mL) to give a pH of 9.2. SPDP (50 mg/mL in dry DMF) was added in four aliquots at 0, 10, 20 and 30 minutes (33.8 mmol total). The reaction mixture was allowed to stand for 2 hours. Ice cold ethanol (2.1 mL) was added and the product left in the freezer overnight. The cloudy product mixture was split into two Eppendorf tubes and centrifuged at maximum speed for 10 minutes. The supernatant was carefully removed and the pellet dissolved in 400 mL $H_2O$. Into this solution was added 2.5 M acetate buffer (20 mL, 2.5M, pH 5.3). TCEP in distilled water (10 mL, 20 mM) was added and the reduction allowed to proceed for 30 minutes at room temperature. Absolute ethanol (1.2 mL) was added and the reaction mixture put in the freezer for 2 hours. The reaction mixture was centrifuged at full speed in the cold room and the precipitated dT(40)-SH oligonucleotide was removed as a pellet. The pellet was dissolved in 200 mL of 50 mM $Na_2HPO_4$ buffer (pH 6.85) containing 20 mM EDTA. The solution was degassed and kept under argon. This solution was then added to the maleimidated dextran chemiluminescer particles (14.2 mg/1.5 mL) (prepared as above) and the reaction mixture allowed to stand overnight. The mixture was centrifuged at 15,000 rpm for 1 hour and the supernatant discarded. The pellet was resuspended in water (2 mL) and centrifuged at 15,000 rpm for 1 hour. The supernatant was discarded and the pellet resuspended in water (2 mL). After a final centrifugation the dt(40)chemiluminescer particles were stored in 2 mL of water solution as a suspension.

Photosensitizer particles having chlorophyll/squarate incorporated therein and having streptavidin immobilized on their surface Latex particles (Seradyn Particle Technology) were treated to incorporate therein chlorophyll-a (Sigma Chemical Company) and tetrabutylsquarate (Sands, Jupiter, Fla.) in the following manner: A dye mixture of chlorophyll-a (2.0 mM) and tetrabutyl squarate (4.0 mM) in benzyl alcohol was prepared. Ethylene glycol (80 mL) was placed in a 125 mL Erlenmeyer flask and warmed to 125° C. on a laboratory hot plate. The dye mixture in benzyl alcohol (8 mL) was then added followed immediately by stock latex suspension (10 mL of 10% solids). Heating was discontinued and the flask and its contents allowed to attain room temperature. After cooling, the mixture was diluted with an equal volume of ethanol and immediately centrifuged at 15,000 rpm for two hours. The bluish-green supernatant was discarded and the pellet suspended in 50 mL of ethanol by sonication. The suspension was centrifuged at 15,000 rpm for one hour and the faintly blue supernatant decanted. The pellet was resuspended in 50% aqueous ethanol (50 mL) by sonication to disperse the particles. Centrifugation was repeated at 15,000 rpm for an hour. The supernatant was decanted and the pellet resuspended in water by sonication. Following a final centrifugation, the particles were resuspended in water to a final volume of 20 mL.

Streptavidin (Aaston, Inc., Wellesley Mass.) was immobilized on the surface of the above latex particles in the following manner:

A suspension of the latex particles (1 mL of 10 mg/mL) was added to an EDAC solution (0.5 mg/mL, 1 mL of 0.02 M phosphate buffer, pH 6.0) cooled to 0° C. The suspension was stirred under argon for 30 minutes. After this time, the suspension was added dropwise into a streptavidin solution (5 mg/mL, 1 mL) in borate buffer (0.2 M, pH 9.0) kept at ~0° C. The suspension was stirred for 1 hour and allowed to warm up to room temperature. Water (1 mL) was added and the mixture centrifuged at 15,000 rpm for 1 hour. The supernatant was discarded and the pellet suspended in water (4 mL) by sonication. The sample was recentrifuged in water (4 mL) by sonication, and after a final centrifugation at 15,000 rpm for 30 minutes, the resultant pellet was suspended in water (5 mL). This gave a 2 mg/mL suspension of streptavidin-latex particles.

C-28 thioxene was prepared as follows:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1

N aqueous NaOH (2×), H$_2$O, and brine, was dried over Na$_2$SO$_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-(C$_{14}$H$_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr an stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with H$_2$O (2×), brine and was dried over MgSO$_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (LSIMS (C$_{42}$H$_{69}$NO$_2$): [M—H]$^+$618.6, $^1$H NMR (250 MHz, CDCl$_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol) ;and the reaction solution was heated at reflux for another 3 hr. The resulting solution was cooled, was made basic with cold 2.5N aqueous NaOH and was extracted with CH$_2$Cl$_2$ (3×). The combined organic layers were washed with saturated aqueous NaHCO$_3$ (2×) and brine, was dried over Na$_2$SO$_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (LSIMS (C$_{44}$H$_{71}$NOS): [M—H]$^+$661.6, $^1$H NMR (250 MHz, CDCl$_3$) was consistent with the expected C-28 thioxene product 2-(4-(N,N-di-(C$_{14}$H$_{29}$)-anilino)-3-phenyl thioxene.

Silicon tetra-t-butyl phthalocyanine was prepared as follows:

Sodium metal, freshly cut (5.0 g, 208 mmol), was added to 300 mL of anhydrous ether in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, as solid started to precipitate. The resulting suspension was evaporated to dryness (house vacuum) and the residue was suspended in water (400 mL) and filtered. The solid was dried (60° C., house vacuum, P$_2$O$_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., P$_2$O$_5$). The solid material was placed in a 1-liter, round bottom flask an concentrated sulfuric acid (500 mL) was added with stirring. The mixture was stirred for 4 hr. at 60° C. and was then carefully diluted with crushed ice (2000 g). The resulting mixture was filtered and the solid wad washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., P$_2$O$_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer an a reflux condenser. The mixture was heated under reflux for 1.5 hr. an then cooled to room temperature. The picoline was distilled off under high vacuum (oil pump at about 1 mm Hg) to dryness. The residue was dissolved in CH$_2$Cl$_2$ and purified using a silica gel column (hexane) to give 10 g of pure product di(tri-n-hexylsilyl)-silicon tetra-t-butyl phthalocyanine as a dark blue solid. (LSIMS: [M—H]$^+$1364.2, absorption spectra: methanol: 674 nm (ϵ180,000): toluene 678 nm, $^1$H NMR (250 MHz, CDCl$_3$): δ: −2.4(m, 12H), −1.3(m, 12H), 0.2–0.9 (m, 54H), 1.8(s, 36H), 8.3(d, 4H) and 9.6 (m, 8H) was consistent with the above expected product.

Example 1A

Detection of amplification products using 5'-biotin labeled primer and a specific reporter sequence in the L segment of the probe DnaJ gene of *E. Coli* (from ATCC, Rockhill Md.) was amplified by PCR using the following primer pairs:

Forward primer:
5'Biotin-TCATGGTTCTGGTCAGGTGCAGAT-3' (SEQ ID NO:2)(3' end binding at 641) (Oligo Etc., Inc.)

Backward primer:
5'TCATGGTTCTGGTCAGGTGCAGATTTAC-CGCGCATACGGAATAGCTTACCGG TCT3' (SEQ ID NO:3)(3' end binding at 1018)

Knot probe P302: an oligonucleotide probe (referred to herein as the "knot probe") where the number denotes the distance, in nucleotides, between the 3'-end of the knot probe to the 5'-end of the target amplicon. The sequence of P302 is 5'CGCTCGAAAATCGG-GAAAAAAAAAAAAAAAAAAAAAAAAT-GACGGGACTTCG C3' (SEQ ID NO:4); knot-N15-L25-N15(D20).

The amplification mixture contained 200 mM dNTPs (dATP, dCTP, dTTP and dGTP, Pharmacia Biotech, Piscataway N.J.), 5 units Pfu polymerase (Stratagene, La Jolla, Calif.), amplification buffer (10 mM Tris-Cl, pH 8.8, 50 mM KCl, 1.5 mM MgCl2, 0.1% Triton X-100 (Pharmacia Biotech), and 7.5 mM DTT), 1 M of each of the primers in a total volume of 100 μl. The mixture also contained 200 nM of knot probe P302. Amplification and formation of the detectable complex of the amplification product and the internal probe was carried out by thermal cycling in a Perkin Elmer cycler as follows: 94° C. (5 min.); 94° C. (1 min.), 72° C. (2 min.), for 25 cycles; 94° C. (5 min.) 55° C. (10 min.). At the end of the thermal cycling, 10 μg of the amplification mixture were mixed with 40 μl of detection buffer (10 mM Tris-Cl, pH 8.8, 50 mM KCl, 1 mM MgCl$_2$, 1 mg/ml dextran 500K, 1 mg/ml BSA, and 300 mM NaCl) containing 6 μg of chemiluminescer particles having incorporated therein the dye dioctadeconylbenzalacridan and having dT40 oligonucleotide immobilized on their surface (prepared as described above), and 8 μg photosensitizer particles having chlorophyll/squarate incorporated therein and having streptavidin immobilized on their surface (prepared as described above). The reaction mixture was incubated at room temperature for 45 min. to permit binding of the appropriate binding partners. The reaction mixture was then irradiated with a 150 watt Xenon lamp for 10 cycles of 1 sec illumination and 1 sec waiting time and the chemiluminescence signal was then read. The association of the two labels, indicating the formation of amplification products, was thus determined by measurement of the signal. The results obtained are summarized in Table 1.

TABLE 1

| Number of target molecules | Chemiluminescence signal |
| --- | --- |
| 1 E5 | 1577 |
| 1 E3 | 599 |
| 1 E2 | 294 |
| 1 E1 | 154 |
| 0 | 35 |

Example 1B

The effect of the length of the L segment in the knot probe on detection of amplification product Conditions for amplification of the E coli K12 DnaJ gene sequence and detection of amplification products were the same as that described in Example 1A, except for systematic changes in the length of the L segment (defined as the linker sequence between the two recognition sequences) of the knot probe. The three knot probes used in this Example 1B were similar to knot probe P302 except for the specified L segment length: knot probe PA:L25, knot probe PB:L20 and knot probe PC:L15.

The results obtained are summarized in Table 2.

TABLE 2

| Number of target | chemiluminescence signal | | |
| --- | --- | --- | --- |
| molecules | PA | PB | PC |
| 1 E7 | 882 | 532 | 516 |
| 1 E5 | 910 | 664 | 366 |
| 1 E3 | 262 | 205 | 122 |
| 1 E2 | 109 | 107 | 69 |
| 1 E1 | 62 | 60 | 45 |
| 0 | 19 | 22 | 20 |

In this example a small improvement in the sensitivity of detection of the amplification product was demonstrated with increased length of the L segment.

Example 1C

The effect of the extent of amplification, i.e. number of amplification cycles, on signal generation Conditions for amplification of the E coli K12 DnaJ gene sequence and detection of amplification products were the same as that described in Example 1A, except for the following profile of thermal cycling, which was employed: 94° C. (5 min.); 94° C. (1 min.);72° C. (2.5 min.) for 30 cycles and 35 cycles, respectively; 94° C. (1 min.); 55° C. (10 min.). Chemiluminescence signal was determined as in Example 1A.

The results obtained are summarized in Table 3.

TABLE 3

| number of target DNA | chemiluminescence signal | |
| --- | --- | --- |
| molecules | 30 cycles | 35 cycles |
| 2000 | 922 | 1717 |
| 200 | 336 | 1095 |
| 20 | 174 | 300 |
| 0 | 33 | 39 |

The chemiluminescence signal observed Increased with increased concentration of amplicon.

Example 1D

Detection of amplification products using two knot probes.

The reactions were carried out as in Example 1A. The amplification mixture contained two knot probes, P302 and P143 (knot-N15-L24-N15(D15) 5'CAACACGACCAT-GACCTAATCCTAATCCTAATCCTAATCG-GATTTTAACGGAC A3' (SEQ ID NO:5). The concentration of the knot probes was varied in the different reaction mixtures to assess the effect of probe concentration on amplicon detectability. The final concentrations of the probes were 300, 200 100, 50 or 25 nM each. For these experiments photosensitizer particles were employed that were prepared in a manner similar to that indicated above with the exception that (GATTAG)7 (SEQ ID NO:6) (The Midland Certified Reagent Company, Midland Tex.) was immobilized on the surface of the photosensitizer particles in place of streptavidin. The chemiluminescer particles with immobilized dT40 were as described above. The following thermal cycling profile was employed: 94° C. (5 min.); 94° C. (1 min.); 72° C. (2.5 min.) for 36 cycles; 94° C. (5 min.); 43° C. (10 min.). The conditions for binding of oligonucleotides of the particles with their respective sequences on the amplicon and the detection and measurement of chemiluminescence signal were as in Example 1A.

The results are summarized in Table 4.

TABLE 4

| No. of target | chemiluminescence signal at various concentrations of knot probes | | | | |
| --- | --- | --- | --- | --- | --- |
| molecules | 300 nM | 200 nM | 100 nM | 50 nM | 25 nM |
| 2000 | 800 | 899 | 896 | 724 | 294 |
| 200 | 378 | 505 | 464 | 363 | 202 |
| 20 | 115 | 211 | 189 | 142 | 72 |
| 0 | 30 | 25 | 30 | 28 | 33 |

As can be seen, amplicon detectability was somewhat dependent on probe concentration, although within an optimal range, signal generation was not strongly dependent on probe concentration. In so far as the probes are not blocked at their 3'-end, these can be extended following hybridization to the amplification product. In later examples, the use of 3'-blocked probes and an exo- polymerase were employed. Under these conditions, the polymerase cannot extend upon the hybridized probe.

Example 1E

Detection of amplification products using various probe Amplification of the DnaJ *E.coli* gene was carried out under the same conditions as in the previous examples. The two probes used were designated P143 and P302 to indicate that these probes hybridize to the amplicon (455 bp) 143 bases and 302 bases, respectively, from its 5'-end. The various P143 probes, namely, Knot probe P143, Omega probe P143 and Linear probe P143, had a common 15 base long sequence at their 3'-end. Similarly, the P302 probes, namely, Knot probe P302, Omega probe P302 and Linear probe P302, had a common 15 base 3'-end. The P143 probes had a (CTAATC)4 oligonucleotide label at the 5'-end of the common recognition sequence (in the L segment) and the P302 probes had a dA25 oligonucleotide label at the 5'-end of the common recognition sequence (in the L segment). The different probes varied in structure with respect to the presence of a second 15 base recognition sequence and the position of this recognition sequence with when hybridized to the target amplicon. For the knot probes, the second recognition sequence was capable of binding nearer to the 5'-end of the amplicon than the first recognition sequence. The omega probes had a second 15 base long recognition sequence which was capable of binding closer to the 3'-end of the amplicon than the first recognition sequence. The linear probes had only a single recognition sequence.

The probes used had the following sequences:

Knot P302 (knot-N15-L24-N15(D20) as shown above)
Knot P143 (knot-N15-L24-N15(D15)):
  5'CMCACGACCATGACCTAATCCTAATC-CTAATCCTAATCGGATTTTAACGGAC A 3' (SEQ ID NO:7).
Omega P302 (omega-N15-L25-N15(D20)):
  5'TTCGATTTCGCCAC-CAAMAAAAAAAAAAAAAAAAAAAAAAT-GATCGGG ACTTCGC 3' (SEQ ID NO:8).
Omega P143 (omega-N15-L24-N15(D14)):
  5'GATGCGGTCTCCAGTCTAATCCTAATC-CTAATCCTAATCGGATTTTAACGGAC A 3' (SEQ ID NO:9).
Linear P302 (linear-N15-L25):
  5'AAAAAAAAAAAAAAAAAAMAAAAAT-TATCGGGACTTCGC 3' (SEQ ID NO:10).
Linear P143 (linear-N15-L24):
  5° CTAATCCTAATCCTAATCCTAATCG-GATTTTAACGGACA 3' (SEQ ID NO:11).

The probes were used in various combinations. In cases in which knot and omega probes were used, the probes were added to the reaction mixtures prior to amplification. In cases where linear probes were used, the probes were added at the end of amplification. Binding of the probes to the amplicon was accomplished by heating the mixture to 94° C for 5 min, followed by incubation at 38° C. for 10 min. The particles used were photosensitizer particles with immobilized (GATTAG)7 and chemiluminescer particles with immobilized dT40, both prepared as described above. The particles were mixed with an aliquot of the amplification mixture and the mixture was incubated at room temperature for 45 min. Chemiluminescence signal was measured as in the previous examples.

Table 5 shows the various combinations of probes used.

TABLE 5

| | P143 | P302 |
|---|---|---|
| 1 | knot-N15-L24-N15(D15) | knot-N15-L24-N15(D20) |
| 2 | knot-N15-L24-N15(D15) | omega-N15-L25-N15(D20) |
| 3 | knot-N15-L24-N15(D15) | linear-N15-L25 |
| 4 | omega-N15-L24-N15(D14) | knot-N15-L24-N15(D20) |
| 5 | omega-N15-L24-N15(D14) | omega-N15-L25-N15(D20) |
| 6 | linear-N15-L24 | knot-N15-L24-N15(D20) |
| 7 | linear-N15-L24 | linear-N15-L25 |

In this set of experiments combinations 1–3 were suitable for the detection of 10 target DNA molecules and combinations 4–7 were suitable for the detection of 104 target DNA molecules in the preamplification sample.

Example 1F

Detection of PCR and ASPP amplification products using a 3'-blocked knot probe.

*E. coli* K12 DnaJ gene sequence was amplified by two different amplification procedures as follows:

5 PCR (polymerase chain reaction) as set forth in Saiki, supra, and ASPP (amplification using a single polynucleotide primer) as set forth in U.S. patent application Ser. No. 08/140,369, supra, the relevant portions of which are incorporated herein by reference.

The following primers were used in the PCR amplification:

Forward PCR primer: 5'biotin-CAAAACAGCGGAAGAGCGTGAAATC 3' (SEQ ID NO:12) (3'-end binds at position 189) (Oligo Etc., Inc.).
Reverse PCR primer: 5'GGATGCGGTCTCCAGT-GTCCA3' (SEQ ID NO:13). (3' binds at position 1191).

The following oligonucleotides were used in ASPP:

ASPP utilized a single primer and a strand switch oligonucleotide (SSO) capable of binding to the same target strand as the primer, at a position closer to the 5'-end of this single strand.

Single primer: 5'-biotin-5'CAAAACAGCGGAAGAGCGTGAAATC3' (SEQ ID NO:14). (3'-end binds at position 189) (Oligo Etc., Inc.) SSO:
  5'CAAAACAGCGGAAGAGCGTGAAATCGGC-CCTGACATGTCAGGGCCGCGGTA CGCTGAT-CAAAGATCCGTGCAACA3' (SEQ ID NO:15) (3'-end binds at position 726).

The composition of the amplification reaction mixtures was similar to that described above in the previous examples. A 3'-ddc-blocked knot probe P484 N15-L24-N15 (D8) with (CTAATC)4 label, prepared as described above, was included in the amplification mixture at the concentrations indicated in Table 6. Knot probe P484 had the following sequence:

5'-TCTGCACCTGACCAGCTTAATCCTAATCCTAA TCTACAG CGAAGAAT*C*-3'(SEQ ID NO:16) (*=phosphorothioate) (prepared using an automated DNA synthesizer until positioning of the thio-modified linkages; manual oxidations were then performed with 0.1 M tetraethylthiuram disulfide (Applied Biosystems, Inc., foster City Calif.) in acetonitrile; remaining bases, if any, were added under normal coupling conditions following the protocol in Applied Biosystems, Inc., User Bulletin, Number 58, February 1991).

The thermal cycling profile for these amplification reactions was as follows: 94° C. (5 min.), 94° C. (0.5 min.); 66°

C. (1 min.), 72° C. (2 min.) for 44 cycles; 94° C. (5 min.), 43° C.(10 min.).

The set of two particles used for the detection of amplification products comprised chemiluminescer particles (dyed with C-28 thioxene, DPP/Eu(TTA)3) with immobilized (GTAATG)7 and photosensitizer particles (dyed with chlorophylla/squarate) with immobilized streptavidin.

The chemiluminescer particles were prepared as follows: DPP/Eu(TTA)$_3$ was prepared by combining 8.69 g of Eu(TTA)$_3$. 3H$_2$O (10 mmoles, Kodak Chemical Company, Rochester N.Y.) and 1.8 g of 1,10-phenanthroline (10 mmoles, Aldrich) in 50 ml of dry toluene and heating to 95° C. in an oil bath for one 1 hour. Toluene was removed under reduced pressure. The ash coloured solid was cystallized from 10 ml of toluene to yeild 10 grams of DPP/Eu(TTA)$_3$. Absorption spectrum: 270 nm (20,000), 340 nm (60,000) (Toluene) 1.R(KBr): Cm$^{-1}$: 3440(s), 1600(s), 1540(s), 1400 (s), 1300(s). Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 3.3 mM C-28 thioxene and 15.5 mM Eu(TTA)$_3$DPP was added; the beads were stirred for 5 minutes more. At this point 1.0 mL of 0.1 N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

The photosensitizer particles were prepared in a manner similar to that described above.

The assay incubation for binding of the appropriate binding partners and the measurement of chemiluminescence signal was as described above in previous examples.

The results obtained are summarized in Table 6.

TABLE 6

| Number of target molecules | Concentration of the 3'-ddc-knot probe | | | | | |
|---|---|---|---|---|---|---|
| | 200 nM | | 100 nM | | 50 nM | |
| | PCR | ASPP | PCR | ASPP | PCR | ASPP |
| 0 | 5258 | 5616 | 5182 | 4328 | 4604 | 4926 |
| 20 | 62576 | 6114 | 76609 | 7846 | 53362 | 42128 |
| 200 | 338032 | 12072 | 379712 | 93012 | 69044 | 69165 |

Example 2
Homogenous detection of amplification products of M. tuberculosis (BCG) (IS6110) gene sequence Example 2A
Single tube amplification and detection of M. tuberculosis (BCG) genomic DNA using two knot Probes ASPP amplification of a genomic M. tuberculosis (BCG) target sequence (IS6110) obtained from C. Green, SRI International, Menlo Park Calif., was carried out using a 22 base long primer and a 67 base long strand switch oligonucleotide (SSO). The resulting amplification product was 495 base pairs long. The amplification was carried out in the presence of two 3'-blocked knot probes (blocked with a propyl group on the 3'-hydroxyl prepared by standard techniques) and the corresponding particles as detailed below:

Primer: 5'GACGGTTGGATGCCTGCCTCGG-3' (SEQ ID NO:17).
SSO: 5'GACGGTTGGA TGCCTGCCTC GGTAAC-CCTG AATTCAGGGT TAGCCACACT TTGCGGGCAC CGTAAAC-3' (SEQ ID NO:18).
Probe A (P274): Knot-N(19)-L(23)-N(19)(D4):
GGGTAGCAGA CCTCACCTAG AGAATCCTAA TCCTAATCCA CAACCACCAG CACCTAACCG G-3' Blocked (3'-Spacer C3 CPG from Glen Research, Sterling Va.) (SEQ ID NO:19).
Probe B (P208): knot-N(20)-L(23)-N(21)(D10):
ACGGATAGGG GATCTCAGTA GACTTTTTTT TTTTTTTTTT TTACGTACTC GACCTGAAAG ACGT-3' Blocked (3'-Spacer C3 CPG from Glen Research) (SEQ ID NO:20).
dNTPs: Deoxynucleotide triphosphates dATP, dTTP, dGTP, dCTP (Pharmacia Biotech).
1× buffer B: 10 mM Tris-HCl pH 8.3, 50 mM KCl, 4.0 mM MgCl$_2$, 0.2 mg/ml acetylated BSA (Gibco BRL, Gaithersburg Md.).
Polymerase: recombinant exo$^-$ Pfu DNA polymerase (Stragene)
Chemiluminescer particles:
Latex particles with chemiluminescer dye C-26 thioxene and Eu(TTA)$_3$ DPP incorporated therein and d(GATTAG)7 oligonucleotide covalently attached through the 5'-end prepared as described above. The C-26 thioxene was prepared in the following manner: Ethyl 5-bromovalerate was condensed with N-methylaniline to give a product that was converted by Kilsmeier-Haak synthesis (DMF/POCl$_3$) to an aldehyde. Benzoin condensation of this aldehyde with benzaldehyde yielded a product which was hydrolyzed with potassium hydroxide and diphenylphosphoryl azide (DPPA). Conversion of the product to the C-26 thoxene was carried out by condensation with mercaptoethanol and TMSCI.
Photosensitizer particles:
Latex particles with a photosensitizer dye silicon tetra-t-butyl phthalocyanine and d(T)$_{40}$ oligonucleotide (Oligo Etc., Inc.) attached covalently through the 5'-end prepared as described above.

The two knot probes had a 3'-end which bound to sequences on the amplicon which were 182 and 373 bases respectively from its 5'-end.

For increased specificity of amplification the well known hot-start technique using HotStart 100 ™ reaction tubes (Molecular Bio-Products, Inc., San Diego, Calif.) was utilized. This was achieved by combining all the reaction components other than the polymerase and sample, in a total volume of 50 µl and sealing this liquid layer with wax (a single wax bead was added to the mixture and the tubes were heated to 70° C. for 2 min. and cooled to room temperature to allow the wax to solidify, thus sealing the liquid ("lower") layer. Prior to initiation of the reaction, the DNA polymerase was mixed with the sample, to a total volume of 50 µl and the mixture added to the reaction mixture. Mixing of the two liquid components was achieved by subjecting the reaction to thermal cycling. The final concentration of the various components in the reaction mixture was as follows:

Primer 0.5 µM; SSO 25 nM; Probes 12.5 nM; Acceptor particles 5.0 µg;
Photosensitizer particles 2.5 µg; dNTPs 200 µM; Buffer B 1×; Polymerase 5 units.

The following thermal cycling profile was employed: 95° C.(2 min); 95° C.(¼ min.), 68° C.(1 min.), 72° C.(1 min.)

x42 cycles; 72° C.(5 min.), 95° C.(2 min.), 50° C.(15 min.), 37° C.(30 min.). This last cycle varied in the experiments listed below.

Examples 2AI and 2AII were carried as above. In Examples 2AIII and 2AIV the last cycle was as follows:

72° C. (5 min.), 95° C.(2 min.), room temperature (2 hr.), 37° C. (30 min.).

The last cycle in Example 2AV was as follows:

72° C. (5 min.), 95° C.(2 min.), room temperature (18 hr.), 37° C. (30 min.).

Chemiluminescence signals were obtained by three cycles of 1 sec illumination (>635 nm) and 1 sec. read (580–630 nm).

The results obtained are summarized in Table 7.

TABLE 7

| Example | Target molecules | Chemiluminescence signal | | |
|---|---|---|---|---|
| 2AI | 0 | 4202 | | |
|  | 20 | 17854 | | |
|  | 100 | 178952 | | |
| 2AII | 0 | 3942 | 3968 | 3682 |
|  | 5 | 4314 | 26878 | 97070 |
|  | 5 | 86956 | | |
|  | 20 | 135236 | | |
| 2AIII | 0 | 4434 | | |
|  | 20 | 259038 | | |
|  | 50 | 263572 | | |
|  | 100 | 253592 | | |
| 2AIV | 0 | 4486 | 4680 | |
|  | 20 | 277118 | 290144 | |
|  | 100 | 215944 | 234686 | |
| 2AV | 0 | 3104 | 3374 | |
|  | 5 | 589658 | 586512 | |
|  | 20 | 603218 | | |

Example 2B

Amplification and detection of M. tuberculosis (BCG) target sequence (1S6110) by either two knot probes or a combination of a knot and a tailed probe.

The target DNA used for this example was an amplicon formed by amplification of M. tuberculosis target sequence (1S6110), similar to that described in previous Example 2A. The amplicon was purified by gel electrophoresis and a dilution containing the specified number of molecules was used in the following experiments. Thus, the target DNA sequence was a stem-loop ds DNA, which was amplified by a single primer. The amplification was carried out in a final volume of 100 µl. The buffer composition, primer, Pfu polymerase and dNTPs were as in previous Example 2A. The sequence of the P85 tailed linear probe (N18-L20) was as follows:

5' GCGTACTCGACCT-GAAAGTTTTTTTTTTTTTTTTTTT 3' (SEQ ID NO:21).

Probes P208 knot and P274 knot were as in previous Example 2A.

The amplification mixture contained two probes, as specified in Table 8, at a final concentration of 10.8 nM each, and two detection particles, a chemiluminesceer particle with (GATTAG)7 and a photosensitizer particle with d(A)40, both prepared as described above. A dilution of a sample with or without target DNA was added to the reaction mixture. Amplification and formation of the detectable complex was carried out by thermal cycling as follows:

95° C. (2 min.); 95° C. (15 sec.), 68° C. (1 min.), 72° C. (1 min.) for 39 cycles; 95° (15 sec), 68° C. (1 min.), 72° C. (5 min.); room temperature (14 hr.); 37° C. (30 min.).

Following this cycling, chemiluminescence was read as in previous Example 2A. The results are summarized in Table 8.

TABLE 8

| DNA target molecules | Probe A | Probe B | Signal |
|---|---|---|---|
| 0 | P208 knot | P274 knot | 4694; 4728 |
| 500 | P208 knot | P274 knot | 45626; 37582 |
| 2000 | P208 knot | P274 knot | 176032; 168692 |
| 0 | P85 tailed linear | P274 knot | 4430; 4514 |
| 500 | P85 tailed linear | P274 knot | 22780; 33486 |
| 2000 | P85 tailed linear | P274 knot | 109548; 115476 |

As can be seen, all combinations of the above probes were suitable for detection of the defined target DNA sequence.

Example 2C

Amplification of M. tuberculosis genomic DNA (IS16110) and ELISA detection using two 3' blocked knot probes An amplification by ASPP was carried out on M. tuberculosis genomic DNA (IS6110) (the "target DNA") in the presence of knot probes. The ASPP amplicon obtained was 650 bp and was derived from M. tuberculosis genomic DNA as in the previous example. The following are the sequence and structure information for the primer and knot probes used in this example:

Primer: 5' ACTGGTAGAGGCGGCGATGGTTGAA 3' (SEQ ID NO:22).

Knot P499: (N(15)-L(24)-N(15)) 5' biotin-AGCAGACCTCACCTACTAATCCTAATC-CTAATCCTAATCACCACCAG CACCTAA 3' phosphate (Oligo Therapeutics, Inc., Wilsonville, Oreg.) (SEQ ID NO:23).

knot P306: (N(15)-L(24)-N15)) 5' digoxin-ATAGGGGATCTCAG-TAAAAAAAAAAAAAAAAAAAAAAAATACTC GACCTGAAAG 3' phosphate (Oligo Therapeutics, Inc.) (SEQ ID NO:24).

Amplification was carried out in a reaction mixture containing 0.5 mM primer, 25 nM of each of knot probe P499 and knot probe P306, 200 µM of the each of the dNTPs, 5 units of exo⁻ Pfu (Stratagene) in buffer (10 mM Tris-HCl pH 8.8, 50 mM KCl, 1.5 mM MgCl2, 7.5 mM DTT and 0.1% Triton X-100). The total reaction mixture was 50 µl. The mixture was subjected to thermal cycling as follows: 95° C. (4 min.); 94° C. (30 sec.), 70° C. (1 min.), 72° C. (2 min.) for 40 cycles; 95° C. (4 min.), 45° C. (15 min.).

A 10 µl aliquot of the amplification reaction mixture was analyzed by ELISA for the presence of amplification product. The assay employed microtiter plates coated with streptavidin ((Pierce Chemical Company, Rockford, Ill.) and anti-digoxigenin Fab fragment-POD conjugate (the "Enzyme Conjugate") (Boehringer Mannheim Corporation, Indianapolis, Ind.). Binding of the two knot probes 499 and 306, one labeled with biotin, the other with digoxin, to one strand of the amplification product, in the last cycle above, results in the association of the two labels, biotin and digoxin, which can be detected by binding to immobilized streptavidin and detection of the digoxin label by the Enzyme Conjugate.

The ELISA protocol was as follows:

1. The streptavidin coated microtiter wells were washed once with 300 µl phosphate buffer pH 7.5, with 0.05% Tween 20.

2. 90 μl of sample buffer (3% BSA, 100 μg/ml calf thymus DNA, 300 mM NaCl, 25% fetal bovine serum and 0.1% Tween-20 in phosphate buffer pH 7.5) was added to each well.
3. 10 μl of amplification reaction mixture was added to each well and the plate was incubated for 1 hr. at 37° C.
4. The wells were washed four times with phosphate buffer (1.7 mM $KH_2PO_4$, 5 mM $Na_2HPO_4$, 150 mM NaCl, pH7.4, Biowhittaker, Walkerville, Mich.) containing 0.05% Tween-20 (250 μl).
5. 100 μl of the Enzyme Conjugate in sample buffer was added to each well and the plate was incubated for 1 hr. at 37° C.
6. The wells were wash four times as in step 4.
7. 100 μl TMB peroxide substrate solution (tetramethylbenzidine, Kirkegaard and Perry, Gaithersburg, Md.) was added to each well and the plate was incubated at room temperature for 30 min.
8. Color development was read at 450 nm.

The results obtained in the absence or presence of approximately 100 molecules of target DNA per reaction are summarized in Table 9.

TABLE 9

| Reaction Mixture | OD at 450 nm |
| --- | --- |
| no target DNA or human DNA | 0.162 |
| no target DNA, 25 ng human DNA | 0.186 |
| no target DNA, 100 ng human DNA | 0.212 |
| target DNA, 25 ng human DNA | 1.399 |
| target DNA, 100 ng human DNA | 1.023 |

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the claims.

What is claimed is:

1. A method for amplifying and detecting a target polynucleotide sequence, which comprises:
   (a) providing in combination (i) a medium suspected of containing said target polynucleotide sequence, (ii) all reagents required for conducting an amplification of said target polynucleotide sequence, and (iii) two oligonucleotide probes that bind to a single strand of the product of said amplification wherein at least one of said probes has two sequences, which are each about 8 to 25 nucleotides in length and which either (i) are non-contiguous and can bind to contiguous or noncontiguous sites on said single strand or (ii) can bind to non-contiguous sites on said single strand,
   (b) subjecting said combination to conditions for amplifying said target polynucleotide sequence, (c) after step (b) subjecting said combination to conditions under which both of said probes hybridize to one of said strands to form a termolecular complex and (d) detecting said complex.

2. The method of claim 1 wherein said reagents comprise two oligonucleotides that bind to said target polynucleotide sequence and an enzyme capable of modifying at least one of said oligonucleotides as a function of the presence of said target polynucleotide sequence.

3. The method of claim 1 wherein said reagents comprise an oligonucleotide primer that binds to and is extended along said target polynucleotide sequence, a nucleotide polymerase and nucleotide triphosphates.

4. The method of claim 1 wherein said reagents comprise (i) two oligonucleotide primers that each bind to and are extended along said target polynucleotide sequence and a sequence complementary to said target polynucleotide sequence, respectively, (ii) a nucleotide polymerase and (iii) nucleotide triphosphates.

5. The method of claim 1 wherein each probe contains a label and said combination further comprises particles that bind to said labels and said detecting comprises detecting agglutination of said particles.

6. A method for amplifying and detecting a target polynucleotide sequence of a polynucleotide analyte, which comprises:

(a) providing in combination a sample suspected of containing a polynucleotide analyte having said target polynucleotide sequence, reagents for amplifying said polynucleotide analyte to produce copies of said target polynucleotide sequence, a first oligonucleotide probe having nucleotide sequences S1 and S2 and a second oligonucleotide probe having sequences S3 and S4 wherein each of S1, S2, S3 and S4 is about 8 to 25 nucleotides in length and wherein the sequences comprising at least one of the probes are linked such that either (i) they are non-contiguous and can bind to contiguous or non-contiguous sites on one of the strands of said copies or (ii) the sites to which they hybridize on one of the strands of said copies are noncontiguous and wherein said probes (i) do not hybridize to said copies during said amplifying and (ii) subsequent to said amplifying, both of said probes can hybridize to one of the strands of said copies, and (iv) each of said probes is comprised of a label that facilitates detection of said probes hybridized to said strands, (b) subjecting said combination to conditions for amplifying said polynucleotide analyte, (c) after step (b) subjecting said combination to conditions under which both of said probes hybridize to one of said strands to form a termolecular complex, and (d) detecting said complex.

7. The method of claim 6 wherein the 3'-terminus of said S1 is linked to the 5'-terminus of said S2 by a linking group comprising a chain of 1 to 200 atoms.

8. The method of claim 7 wherein said chain comprises from 1 to 40 nucleotides or nucleotide analogs.

9. The method of claim 7 wherein at least a portion of said inking group is an oligonucleotide label.

10. The method of claim 6 wherein the 3'-terminus of said S1 is linked to the 5'-terminus of said S2 by a linking group and the 3'-terminus of said S3 is linked to the 5'-terminus of said S4 by a linking group, each of said linking groups comprising from 0 to 40 nucleotides or nucleotide analogs.

11. The method of claim 6 wherein detection of said complex comprises association of said complex with particles.

12. The method of claim 11 wherein said detection comprises detecting agglutination of said particles.

13. The method of claim 6 wherein said label is an oligonucleotide label.

14. The method of claim 6 wherein said S1 hybridizes to a site on said copies that lies 5' of the hybridization site of said S2 on said copy wherein the 3'-end of said S1 is linked to the 5'-end of said S2.

15. The method of claim 6 wherein S1 and S2 are linked by a nucleotide linking group and S3 and S4 are linked by a nucleotide linking group.

16. The method of claim 15 wherein each of said linking groups comprises an oligonucleotide label.

17. The method of claim 16 wherein said combination comprises oligonucleotides N1 and N2 that are each respectivley complementary to one of said oligonucleotide labels wherein said N1 and N2 are each labeled with a reporter group.

18. The method of claim 17 wherein said N1 is associated with a particle having a photosensitizer associated therewith and said N2 is associated with a particle having a chemiluminescent compound associated therewith.

19. A method of detecting a target polynucleotide containing a target polynucleotide sequence wherein all reagents required for said method are first combined with said target polynucleotide, said method comprising:

(a) dissociating said target polynucleotide sequence into single strands when said target polynucleotide sequence is double stranded, (b) hybridizing an oligonucleotide primer to the 3'-end of each of said single strands, (c) extending said primer hybridized to each of said single strands along the single strand to produce a copy of said target polynucleotide sequence, (d) dissociating said copy into single strands, (e) hybridizing two oligonucleotide probes to one of said single strands wherein at least one of said probes is comprised of two sequences that hybridize with one of said single strands, wherein said sequences either (i) are non-contiguous and can bind to contiguous or non-contiguous sites on said strand or (ii) the sites on said strand to which said sequences hybridize are non-contiguous, (f) detecting the binding of both of said probes to said single strand, the presence thereof being related to the presence of said target polynucleotide.

20. The method of claim 19 wherein each of said probes is comprised of a label.

21. The method of claim 19 wherein at least one of said probes is bound to or can become bound to a particle.

22. The method of claim 21 wherein said particle is comprised of a photosensitizer.

23. The method of claim 21 wherein said particle is comprised of a luminescent compound.

24. The method of claim 19 wherein each of said probes is comprised of two sequences that hybridize with said single strand, said sequences and/or said sites on said strand to which said sequences hybridize being non-contiguous.

25. The method of claim 19 wherein each of said probes is comprised of an oligonucleotide label.

26. The method of claim 25 wherein said detecting comprises binding of nucleotides N1 and N2, respectively, to said oligonucleotide label of each of said probes wherein said N1 is bound to a first label and said N2 is bound to a second label.

27. The method of claim 26 wherein said first label is comprised of a photosensitizer.

28. A method for detecting a target sequence of a target polynucleotide ("target sequence"), said method comprising:
(a) amplifying said target sequence by a method comprising:
(i) hybridizing to the 3'-end of said target sequence a first oligonucleotide primer ("first primer"),
(ii) extending, in the presence of a polymerase and nucleotide triphosphates, said first primer along at least said target sequence to produce an extended first primer, said first primer hybridizing to, and being extended along, (1) said extended first primer or (2) an extended second oligonucleotide primer ("second primer") wherein said extended second primer results from the extension of a second primer that hybridizes to and is extended along a polynucleotide that is complementary (complementary polynucleotide) to said target sequence,
(iii) dissociating said extended first primer from said target sequence,
(iv) hybridizing, to the 3'-end of said extended first primer, said first or said second primer,
(v) extending said first or said second primer along said extended first primer,
(vi) dissociating said extended first primer or said extended second primer from said extended first primer,
(vii) hybridizing, to the 3'-end of said extended first or said extended second primer, said first primer, and
(viii) repeating steps (v)–(vii), and
(b) detecting said extended first primer and/or said extended second primer by means of a first oligonucleotide probe having nucleotide sequences S1 and S2 and a second oligonucleotide probe having sequences S3 and S4, wherein S1, S2, S3 and S4 are each about 10 to 20 nucleotides in length wherein the sequences comprising at least one of the probes are linked such that its two sequences either (i) are non-contiguous and can bind to contiguous or non-contiguous sites on one of said extended primers or (ii) hybridize to sites on one of said extended primers that are noncontiguous and wherein said probes (A) are present during said amplifying, (B) do not hybridize to said extended first and/or second primers during said amplifying of step (a) and (C) do not interfere with said amplifying of step (a) and (D) subsequent to said amplifying of step (a), both of said probes can hybridize to one of said extended first and/or said extended second primers to form a termolecular complex, and (E) one or both of said probes contains a label that facilitates detection of said probes hybridized to said extended first and/or said extended second primers.

29. The method of claim 28 wherein the repeating of steps (v)–(vii) is achieved by repeated temperature cycling.

30. The method of claim 28 wherein said target polynucleotide is DNA.

31. The method of claim 28 wherein only said first primer is used and said target sequence contains at its 5'-end at least a 10-base sequence hybridizable with a sequence at the 3' end of said target sequence to which said first primer hybridizes.

32. The method of claim 28 wherein said first and said second primers are different and said extended first primer is a template for said second primer and said extended second primer is a template for said first primer.

33. The method of claim 28 wherein the 3'-terminus of said S1 is linked to the 5'-terminus of said S2 by a linking group comprising from 0 to 40 nucleotides or nucleotide analogs.

34. The method of claim 28 wherein the 3'-terminus of said S1 is linked to the 5'-terminus of said S2 by a linking group and the 3'-terminus of said S3 is linked to the 5'-terminus of said S4 by a linking group, each of said linking groups comprising from 0 to 40 nucleotides or nucleotide analogs.

35. The method of claim 28 wherein detection of said complex comprises association of said complex with particles.

36. The method of claim 35 wherein said detection comprises detecting agglutination of said particles.

37. The method of claim 28 wherein said label is an oligonucleotide label.

38. The method of claim 28 wherein said sequences comprising at least one of the probes are linked by a linking group, at least a portion of said linking group comprising an oligonucleotide label.

39. The method of claim 38 wherein each of said probes comprises an oligonucleotide label and said detecting of step (b) comprises the use of nucleotides N1 and N2, each respectively complementary to one of said oligonucleotide labels, wherein said N1 and N2 are each labeled with a reporter molecule.

40. The method of claim 39 wherein said N1 is associated with a particle having a photosensitizer associated therewith and said N2 is associated with a particle having a chemiluminescent compound associated therewith.

41. A kit for use in an amplification and detection of a target polynucleotide sequence of a target polynucleotide, said kit comprising in packaged combination:
(a) an oligonucleotide primer which hybridizes to said target polynucleotide and is extended along said target polynucleotide sequence to produce extended oligonucleotide primer,
(b) nucleoside triphosphates,
(c) a nucleotide polymerase,
(d) a first oligonucleotide probe having nucleotide sequences S1 and S2, and
(e) a second oligonucleotide probe having sequences S3 and S4,
wherein S1, S2, S3 and S4 are each about 10 to 20 nucleotides in length and
wherein the sequences comprising at least one of said first or said second oligonucleotide probes are linked such that either (i) they are non-contiguous and can bind to contiguous or non-contiguous sites on said extended polynucleotide primer or a complementary sequence thereto or (ii) the sites to which they hybridize on said extended polynucleotide primer or a complementary sequence thereto are noncontiguous, and
wherein said probes have the characteristics that they (i) do not hybridize to said extended oligonucleotide primer during said amplification and (ii) subsequent to said amplification, both of said first and second oligonucleotide probes can hybridize to said extended oligonucleotide primer or said complementary sequence, and (iii) one or both of said probes contain a label that facilitates detection of said probes hybridized to said extended oligonucleotide primer or said complementary sequence.

42. The kit of claim 41 wherein the 3'-terminus of said S1 is linked to the 5'-terminus of said S2 by a nucleotide linking group.

43. The kit of claim 42 wherein at least a portion of said nucleotide linking group is an oligonucleotide label.

44. The kit of claim 41 wherein one of said probes is associated with a particle.

45. The kit of claim 44 wherein said particle is bound to or binds to said probe.

46. The kit of claim 41 wherein said label is an oligonucleotide label.

47. The kit of claim 41 wherein S1 and S2 are linked by a nucleotide linking group and S3 and S4 are linked by a nucleotide linking group.

48. The kit of claim 47 wherein said linking groups comprise oligonucleotide labels.

49. The kit of claim 48 comprising nucleotide N1 and N2 each complementary to one of said oligonucleotide labels wherein said N1 and N2 are each labeled with a reporter molecule.

50. The kit of claim 49 wherein said N1 is associated with a particle having a photosensitizer associated therewith and said N2 is associated with a particle having a chemiluminescent compound associated therewith.

51. The kit of claim 41 comprising a second oligonucleotide primer.

52. A kit for detection of a target polynucleotide sequence, said kit comprising in packaged combination reagents for conducting an amplification of said target polynucleotide sequence and two labeled oligonucleotide probes that bind to the product of said amplification of said target polynucleotide sequence wherein at least one of said probes has two sequences that are each about 10 to 20 nucleotides in length and that are non-contiguous and can bind to contiguous or non-contiguous sites on a single strand of said product.

53. A method for amplifying and detecting a target polynucleotide sequence, which comprises:

(a) providing in combination a sample suspected of containing a target polynucleotide having said target polynucleotide sequence, reagents for amplifying said target polynucleotide sequence to produce copies thereof, a first oligonucleotide probe and a second oligonucleotide probe wherein said probes (i) do not hybridize to said copies during said amplifying and (ii) do not interfere with said amplifying and (iii) subsequent to said amplifying, both of said probes can hybridize to one the strands of said copies, and wherein at least one said probes is associated with a particle, (b) subjecting said combination to conditions for amplifying said target polynucleotide sequence to produce said copies, (c) thereafter subjecting said combination to conditions under which both of said probes hybridize to one of said strands and result in agglutination of said particles, and (d) detecting said agglutination wherein the presence of agglutination indicates the presence of said target polynucleotide sequence.

* * * * *